(12) United States Patent
Magaletta

(10) Patent No.: US 11,062,584 B1
(45) Date of Patent: Jul. 13, 2021

(54) SYSTEM AND METHOD OF MONITORING AN OFFENDER, DEFENDANT, OR POTENTIAL VICTIM

(71) Applicant: Robert Magaletta, Covington, LA (US)

(72) Inventor: Robert Magaletta, Covington, LA (US)

(*) Notice: Subject to any disclaimer, the term of this patent is extended or adjusted under 35 U.S.C. 154(b) by 0 days.

(21) Appl. No.: 16/716,091

(22) Filed: Dec. 16, 2019

Related U.S. Application Data

(60) Provisional application No. 62/780,708, filed on Dec. 17, 2018.

(51) Int. Cl.
| | |
|---|---|
| *G08B 21/02* | (2006.01) |
| *G04G 21/02* | (2010.01) |
| *G04G 21/06* | (2010.01) |
| *G04G 21/04* | (2013.01) |
| *H04W 4/90* | (2018.01) |
| *A61B 5/024* | (2006.01) |
| *A61B 5/00* | (2006.01) |
| *A61B 5/117* | (2016.01) |
| *H04W 4/029* | (2018.01) |
| *G04B 37/08* | (2006.01) |
| *G01S 19/16* | (2010.01) |

(52) U.S. Cl.
CPC ...... *G08B 21/0269* (2013.01); *A61B 5/02438* (2013.01); *A61B 5/117* (2013.01); *A61B 5/681* (2013.01); *G04G 21/025* (2013.01); *G04G 21/04* (2013.01); *G04G 21/06* (2013.01); *G08B 21/0261* (2013.01); *G08B 21/0288* (2013.01); *H04W 4/029* (2018.02); *H04W 4/90* (2018.02); *G01S 19/16* (2013.01); *G04B 37/08* (2013.01)

(58) Field of Classification Search
CPC combination set(s) only.
See application file for complete search history.

(56) References Cited

U.S. PATENT DOCUMENTS

| | | | |
|---|---|---|---|
| 7,015,817 | B2 | 3/2006 | Copley et al. |
| 7,123,141 | B2 | 10/2006 | Contestabile |
| 7,619,533 | B2 | 11/2009 | Crucilla |
| 8,514,070 | B2 | 8/2013 | Roper et al. |
| 8,831,627 | B2 | 9/2014 | Aninye et al. |
| 8,866,869 | B2 | 10/2014 | Fennell |
| 9,218,814 | B2 | 12/2015 | Xiong |
| 9,801,058 | B2 | 10/2017 | Tali et al. |
| 2005/0040944 | A1 | 2/2005 | Contestabile |
| 2008/0012760 | A1 | 1/2008 | Derrick et al. |

(Continued)

*Primary Examiner* — Travis R Hunnings
(74) *Attorney, Agent, or Firm* — Garvey, Smith & Nehrbass, Patent Attorneys L.L.C.; Charles C. Garvey, Jr.; Seth M. Nehrbass

(57) ABSTRACT

A method and apparatus for monitoring an offender or defendant or potential victim wherein in one embodiment the apparatus comprises a smartwatch which may include the following features: two way voice communication, software to permit biometric identification of the individual, a tamper resistant band, location tracking, a casing which is waterproof, a wireless telephone communicator, one or more sensors (for example, a light sensor or a heart rate sensor), a wireless charger, a touch screen, a microphone, and a camera. In another embodiment, the smartwatch includes a panic alert button. The apparatus allows the enrollee or wearer of the device to be monitored by a third party and allows communication between the third party and the enrollee or wearer of the device.

20 Claims, 16 Drawing Sheets

(56) References Cited

U.S. PATENT DOCUMENTS

| | | | |
|---|---|---|---|
| 2010/0267361 A1* | 10/2010 | Sullivan | H04W 4/02 455/404.2 |
| 2012/0050532 A1 | 3/2012 | Rhyins | |
| 2014/0002575 A1 | 1/2014 | Fennell | |
| 2015/0305655 A1* | 10/2015 | Sharpe | G09B 19/0038 2/67 |
| 2016/0158602 A1* | 6/2016 | Lee | A63B 24/0062 700/91 |
| 2016/0302706 A1* | 10/2016 | Richards | A61B 5/14532 |
| 2017/0162031 A1 | 6/2017 | Drolshagen et al. | |
| 2018/0049028 A1* | 2/2018 | Tali | G06F 21/40 |
| 2020/0160720 A1* | 5/2020 | Rivera | G08G 1/005 |

* cited by examiner

SYSTEM AND METHOD OF MONITORING AN OFFENDER, DEFENDANT, OR POTENTIAL VICTIM

CROSS-REFERENCE TO RELATED APPLICATIONS

This application claims priority benefit to my U.S. Provisional Patent Application No. 62/780,708, filed 17 Dec. 2018, which is herein incorporated by reference.

STATEMENT REGARDING FEDERALLY SPONSORED RESEARCH OR DEVELOPMENT

Not applicable

REFERENCE TO A "MICROFICHE APPENDIX"

Not applicable

BACKGROUND OF THE INVENTION

1. Field of the Invention

The present invention relates to an apparatus and method for monitoring an offender, defendant, or potential victim. In one embodiment, the present invention monitors an offender who has an upcoming court date (e.g., hearing or trial) wherein the offender pays an agreed fee to a first entity that is a monitoring entity. The first entity monitors the offender via one or more methods after the offender is released from jail. Based upon an agreed formula, the fee is shared with a second entity that is a law enforcement entity. If the offender fails to appear for a scheduled court date, the first entity learns of the failure to appear via remote monitoring, such as that done by a "smart" device (e.g., use of a "smart" phone or "smart" watch). The first entity then notifies the second entity or law enforcement entity who then apprehends the offender.

2. General Background of the Invention

After an arrest, offenders are in some cases released until they are obligated to appear in court before a judge or attend a hearing that is related to their arrest/accused crime.

When these defendants or offenders do not show for their appearance or hearing, there is a need to have a notification of such failure to appear. There is also a need to apprehend the offender after such a failure to appear.

The following are incorporated herein by reference:
U.S. Pat. Nos. 7,015,817; 7,123,141; 7,619,533; 8,514,070; 8,831,627; 8,866,869; 9,218,814; and 9,801,058; U.S. Patent Application Publication Nos.: 2005/0040944; 2008/0012760; 2010/0267361; 2012/0050532; 2014/0002575; 2017/0162031; and 2018/0049028.

Additionally, the following websites are also incorporated by reference:
http://www.laipac.com/s911-braceletst.html and
http://www.laipac.com/s911enforcer.html.

BRIEF SUMMARY OF THE INVENTION

The method and apparatus of the present invention solves the problems confronted in the art in a simple and straightforward manner. What is provided is a method and apparatus that helps solve some of the challenges that agencies are faced with regarding the monitoring of offenders. The method of the present invention provides an improved method wherein a defendant pays to enroll in a program featuring a first, monitoring entity and a second entity, such as a law enforcement entity. As part of the method, a percentage of the revenue received by the monitoring entity is paid according to an agreed formula to law enforcement and/or a prosecutor's office for each parish/county in which the program is implemented.

As part of the method, law enforcement will use the funds to cover the cost to enroll defendants into the monitoring program. Law enforcement will arrest defendants who fail to comply with the terms of their release or fail to appear for court. This method can also include sharing of the agreed fee with a law enforcement agency (e.g. sheriff or police department and/or a prosecutor's office).

Defendants will be monitored when released from jail. These methods include Telephony Network, GPS tracking, Wi-Fi tracking, mobile application, automated notifications, network triangulation, interactive voice interview.

The present invention features a biometric voice verification system that tracks offenders/defendants via an app on a "smart" device, such as a smartphone (e.g., iPhone or Android) or the ShadoWatch. The system can be set up to ensure court compliance, sending notifications, such as court date reminders, automatically to the defendants. In another embodiment, the present invention utilizes a smartwatch as the tracking device. In various embodiments, the participant or enrollee can respond to notifications via the app. In various embodiments, the participant or enrollee can make payments.

If a defendant does not show up for court, law enforcement officials can locate a defendant or the offender via the defendant's "smart" device (e.g., smartphone or smartwatch) and/or go back and review historical location data in attempts to apprehend the defendant.

The defendants are billed directly for these services. In one embodiment, the fee collected from the accused or defendant is shared according to an agreed formula with a law enforcement agency (e.g., local jail or sheriff's office).

Telephony network can include 2-way voice biometrics, cellular network, location verification, interactive review (self-report) or notifications via push, text, telephony (e.g., with ability to conference a live call).

Continuous GPS tracking can be tracked via ankle or wrist devices.

Mobile applications include GPS location verification, cellular network location verification, facial recognition, interactive interview (self-report), Bluetooth connected ankle or wrist device, live video as well as notifications via push, text (SMS) and telephony (with the ability to conference a live call).

The present invention features automated notification to ensure court compliance and includes, push, text (SMS), court date reminders with custom notification such as court date change, etc.

The present invention can also feature automated systems for collecting funds directly from the defendant.

In one embodiment of the present invention, an officer can track a defendant's whereabouts and compliance history by either automated or manual intervention.

The method of the present invention can include revenue sharing with a law enforcement agency and/or prosecutor's office, for example, and can include using law enforcement to arrest defendants.

If a defendant does not show up for court, law enforcement officials can locate offenders via their smart device and the method of the present invention and/or go back and review historical location data in attempts to apprehend them.

The method of the present invention features a biometric platform that is a powerful and complete community supervision package. The method of the present invention includes a variety of comprehensive compliance services that can be implemented individually, or as a complete solution, with no geographical restrictions.

A preferred embodiment of method of the present invention provides the following core elements and services:
1) voice verification;
2) fingerprint;
3) facial recognition; and
4) mobile application.

The core services of the method of the present invention include, for example, Location Based Services (LBS), Self-Report Interview (SRI), Notifications with optional delivery verification, Random Drug Test (RDT) notifications with message verification delivery, Sobriety, Offender Pay Solutions (OPS), Caseload Management (CLM), Officer Mobile App (OMA), and Travel Pass.

The present invention includes a method of supervising an offender or defendant who has been arrested or incarcerated and then released. Preferably, the method comprises the steps of:
a) the offender or defendant paying to a first monitoring entity an enrollment fee so that the offender or defendant becomes an enrollee;
b) wherein in step "a" the enrollee has a mobile device or land line device having a camera and that is able to receive messages and/or telephone calls from the first monitoring entity;
c) the enrollee receiving from the first monitoring entity a communication;
d) wherein in step "c" the communication requires that the enrollee film himself or herself using the camera of his or her land line or mobile device;
e) the monitoring entity selecting a method of identifying the enrollee by optionally using voice recognition or facial recognition; and
f) the monitoring entity notifying a second entity that is a law enforcement entity if the enrollee does not answer the communication of step "c" or is not properly identified by the voice recognition or facial recognition of step "e";
g) after step "f" the second entity apprehending the enrollee; and
h) wherein the fee of step "a" is shared by the first and second entities according to an agreed formula.

Preferably, the enrollee has a curfew schedule and the communication of step "c" is a curfew management call.

In one preferred embodiment, the communication is at a random time selected by the first monitoring entity. In other preferred embodiments, the communication is at an agreed time.

Preferably, in step "c" there are multiple communications before step "f". Preferably, these communications are at random times.

Preferably, there are multiple enrollees using the same land line or mobile device and wherein an identification pin number or caller identification verifies which enrollee is called.

Preferably, after a failure of voice recognition or facial recognition, an enrollee is able to repeat the voice recognition or facial recognition by an enrollee initiated communication.

Preferably, the enrollee location is determined during step "c".

Preferably, location is used to confirm that the enrollee is within a telephone service area during steps "c"-"e".

Another preferred method of the present invention for supervising an offender or defendant who has been arrested or incarcerated and then released, comprises the steps of:
a) the offender or defendant paying to a first monitoring entity an enrollment fee so that the offender or defendant becomes an enrollee;
b) wherein in step "a" the enrollee has a mobile device or land line device having a camera and that is able to receive messages and/or telephone calls from the first monitoring entity;
c) the enrollee initiating a communication with a first monitoring entity using the land line or mobile device, wherein the first entity is optionally able to identify the enrollee by caller identification;
d) wherein in step "c" the communication requires that the enrollee film himself or herself using the camera of his or her land line or mobile device;
e) the monitoring entity selecting a method of identifying the enrollee by optionally using voice recognition or facial recognition; and
f) the monitoring entity notifying a second entity that is a law enforcement entity if the enrollee does not answer the communication of step "c" or is not properly identified by the voice recognition or facial recognition of step "e";
g) after step "f" the second entity apprehending the enrollee; and
h) wherein the fee of step "a" is shared by the first and second entities according to an agreed formula.

Preferably, in step "c" there are multiple communications and the first entity provides to the enrollee a schedule for said communications.

Preferably, the communications can be in any language.

Preferably, the enrollee is required to answer questions during one or more of said communications. In some preferred embodiments, the questions are via text message. In these embodiments, it is preferable for the enrollee to be able to answer the questions via text message.

Preferably, after an initial interview, the enrollee is sent an alert that requests a communication from the enrollee to complete the interview with a communication and wherein the alert cannot be dismissed and prevents use of the mobile device until the enrollee initiates the call.

In some preferred embodiments, the communication of step "c" is a text message.

In some preferred embodiments, the communication of step "c" is a notification. The notification is preferably an email, text to speech voice with verification, text to speech without voice verification, SMS, voicemail, or text to speech paired with SMS.

Another preferred method of the present invention for of supervising an offender or defendant who has been arrested or incarcerated and then released, comprises the steps of:
a) the offender or defendant paying to a first monitoring entity an enrollment fee so that the offender or defendant becomes an enrollee;
b) wherein in step "a" the enrollee has a mobile device or land line device having a camera and that is able to receive messages and/or telephone calls from the first monitoring entity;
c) the enrollee receiving from the first monitoring entity a communication that is a drug test notification;

d) wherein in step "c" the communication requires that the enrollee self-identify and/or film himself or herself using the camera of his or her land line or mobile device;

e) the monitoring entity selecting a method of identifying the enrollee by optionally using voice recognition or facial recognition; and f) the monitoring entity notifying a second entity that is a law enforcement entity if the enrollee does not answer the communication of step "c" or is not properly identified by the voice recognition or facial recognition of step "e";

g) after step "f" the second entity apprehending the enrollee; and h) wherein the fee of step "a" is shared by the first and second entities according to an agreed formula.

Preferably, in step "c" there are multiple communications before step "f".

Preferably, the enrollee is identified by voice without voice biometric verification, voice with biometric verification, text to speech (TTS), SMS (text message(s)), uploaded way file in any language, or text to speech and SMS simultaneously.

Preferably, the enrollee is provided with a breathalyzer device and after step "c" is required to use the breathalyzer device to provide a value for the enrollee's alcohol consumption. Preferably, the value is transmitted to the first monitoring entity via a REST API call from the BACtrack® device which requests and receives responses via HTTP protocol.

A preferred device of the present invention is a smart watch/device for locating, tracking and/or monitoring a person. Preferably, the device includes at least the following:
  a global positioning system (GPS) receiver;
  a wireless telephone communicator;
  a casing which is water resistant;
  a light sensor;
  a heart rate sensor;
  a tamper proof band;
  a wireless charger;
  a screen;
  a speaker;
  a microphone;
  software to permit biometric identification of individual wearing device;
  software to permit communication between device and third party or third party device; and
  a camera.

Preferably, the casing is waterproof.
Preferably, the casing is waterproof to at least 3 meters.
Preferably, the casing can work for at least 30 minutes while under up to 15 cm of water.
Preferably, the screen comprises an interactive interface.
Preferably, the communication is voice communication.
Preferably, the communication is not voice communication.

The methods of the present invention can be carried out with a watch of the present invention, the watch comprising:
  a global positioning system (GPS) receiver;
  a wireless telephone communicator;
  a casing which is water resistant;
  a light sensor;
  a heart rate sensor;
  a tamper proof band;
  a wireless charger;
  a screen;
  a speaker;
  a microphone;
  software to permit biometric identification of individual wearing device;
  software to permit communication between device and third party or third party device; and
  a camera.

The methods of the present invention can be carried out with a watch of the present invention, the watch comprising:
  a global positioning system (GPS) receiver;
  a wireless telephone communicator;
  a casing which is water resistant;
  a light sensor;
  a heart rate sensor;
  a tamper proof band;
  a wireless charger;
  a screen;
  a speaker;
  a microphone;
  software to permit biometric identification of individual wearing device;
  software to permit communication between device and third party or third party device; and
  a camera.

The methods of the present invention can be carried out with a system of the present invention, the system comprising:
  a first monitoring entity;
  a second monitoring entity;
  a communications network; and
  a communication device.

The communication device of the system preferably comprises a watch. Wherein the watch has at least the following:
  a global positioning system (GPS) receiver;
  a wireless telephone communicator;
  a casing which is water resistant;
  a light sensor;
  a heart rate sensor;
  a tamper proof band;
  a wireless charger;
  a screen;
  a speaker;
  a microphone;
  software to permit biometric identification of individual wearing device;
  software to permit communication between device and third party or third party device; and
  a camera.

The methods of the present invention can be carried out with a system of the present invention, the system comprising:
  a computer network;
  a first monitoring entity;
  a second monitoring entity;
  a communications network; and
  a communication device,
  wherein the communication device is a watch comprising:
  a global positioning system (GPS) receiver;
  a wireless telephone communicator;
  a casing which is water resistant;
  a light sensor;
  a heart rate sensor;
  a tamper proof band;
  a wireless charger;
  a screen;
  a speaker;
  a microphone;
  software to permit biometric identification of individual wearing device;

software to permit communication between device and third party or third party device; and a camera.

The present invention also includes a system to prevent kidnapping, the system comprising:
 a computer network;
 a central monitoring facility;
 a communications network; and
 a communication device,
 wherein the mobile device is a watch comprising:
 a global positioning system (GPS) receiver;
 a wireless telephone communicator;
 a casing which is water resistant;
 a light sensor;
 a heart rate sensor;
 a tamper proof band;
 a wireless charger;
 a screen;
 a speaker;
 a microphone;
 software to permit biometric identification of individual wearing device;
 software to permit communication between device and third party or third party device;
 a camera; and
 a panic alert button.

In this system, preferably the device establishes communication with the central monitoring facility when a triggering event takes places. Preferably, the triggering event comprises an alert generated by the kidnapping victim, a detection of tampering by the device, or detection that the victim or device is outside of a pre-determined safe zone. Preferably, the establishment of communication between the device and the central monitoring facility alerts trained operators of a potential hostage attempt/kidnapping in progress. Preferably, once communication is established, a central station operator asks the victim if they are okay via the two-way voice function of the device and if the victim responds they are okay, the operator will respond by asking them what their secret passphrase is; wherein the victim has the option of responding with the phrase associated with a false alarm that all is okay or a phrase associated with an actual kidnapping or hostage event; wherein if the phrase stated by the victim matches the passphrase on file, the operator will respond by thanking the victim and stating that they have verified the passphrase, and to have a good day; wherein authorities are dispatched once victim responds with passphrase on file.

A device of the present invention is preferably a smart watch/device for locating, tracking and/or monitoring a person. Preferably, the device comprise:
 a global positioning system (GPS) receiver;
 a wireless telephone communicator;
 a casing which is water resistant;
 a tamper proof band;
 a charger;
 a screen;
 a speaker;
 a microphone;
 software to permit biometric identification of individual wearing device;
 software to permit communication between device and third party or third party device; and
 a camera.

Preferably, the casing can work for at least work for at least 30 minutes while under up to 1 m of water. Preferably, the device meets the standards of an IP67 waterproof rating.

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings, wherein like reference numerals denote like elements and wherein.

DETAILED DESCRIPTION OF THE INVENTION

Figure 1:
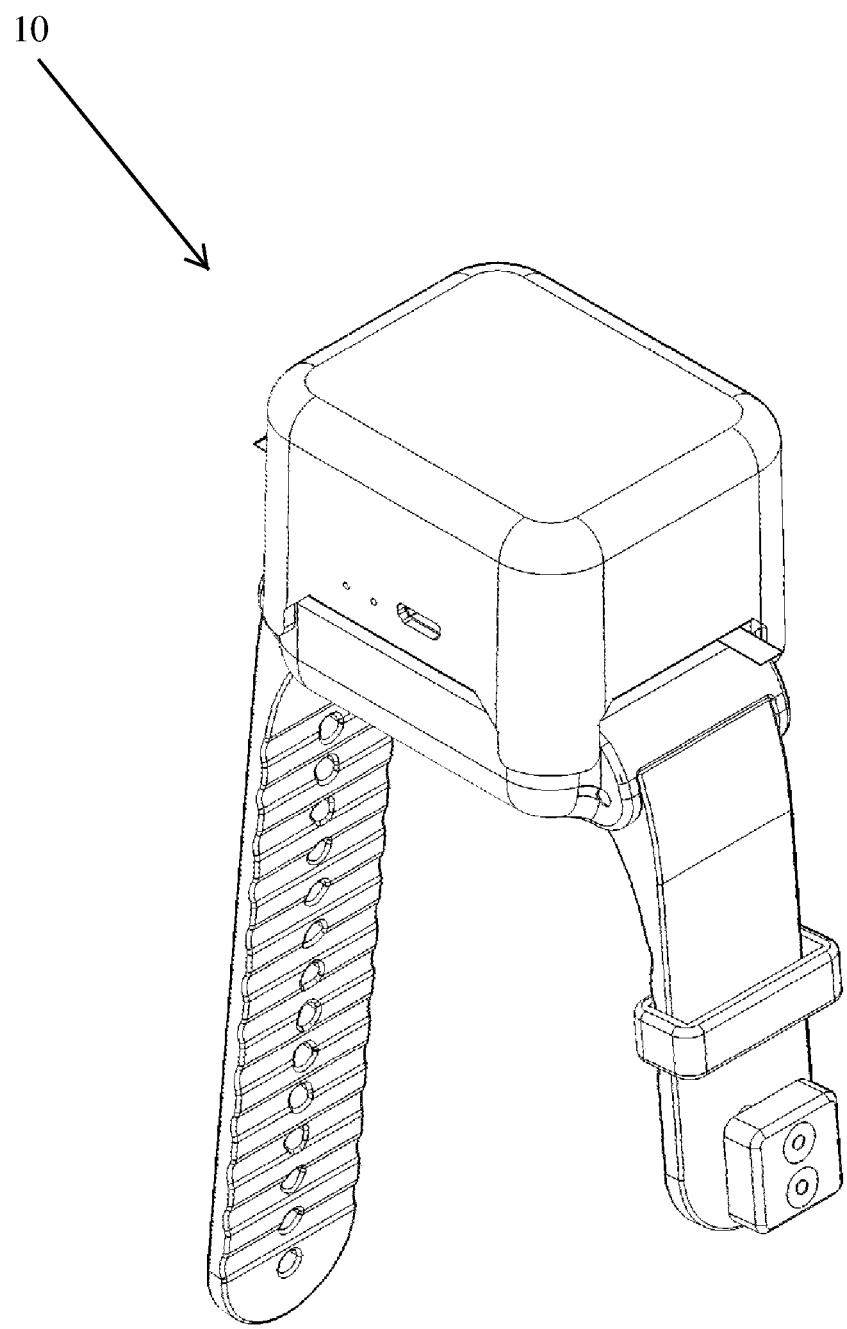
FIG. 1 is a side perspective view of a watch embodiment of the present invention wherein the charging station is attached to the watch.

The curfew management application of the present invention allows the user to verify whether a defendant, offender, or enrollee is at a designated location at a specific time. In one embodiment of the present invention, the curfew management application uses voice verification and facial recognition during inbound/outbound curfew calls to positively identify an enrollee. The curfew management application allows the user (such as a law enforcement official, for example) to schedule random calls or push notifications at a desired frequency. These calls or push notifications may be placed outbound to the enrollee or the enrollee may be required to call into the system from the designated location. The application uses a feature that retrieves caller ID information and may alert the user if the enrollee is calling in from an unauthorized phone number. In one embodiment, the user may be notified if the enrollee fails to successfully complete inbound/outbound curfew calls due to no answer, hang ups, busy signals, and voicemails.

Utilizing curfew management and the curfew management application of the present invention enables a law enforcement agency to efficiently monitor the whereabouts of enrollees. Curfew management provides the ability to create a set or random curfew schedule. The curfew management application of the present invention enables an agency to:

1) schedule random curfew calls during a specific time frame on a certain day;
2) schedule random outbound curfew calls during a daily, weekly, monthly, or random period;
3) modify a curfew schedule;
4) send random push notifications to the enrollee's smart phone to initiate a curfew call;
5) use caller ID feature that detects if the enrollee is attempting to place an inbound call from an unauthorized phone number or use call forwarding;
6) positively identify the enrollee by using voice verification or facial recognition technology;
7) enable the enrollee to perform a voice verification request via the telephony network and the option to perform a verification request using a Wi-Fi data network;
8) easily access reports of all tracking history;
9) provide instant, daily, or weekly automated user email alerts of non-compliant calls;
10) reduce false non-compliance results by specifying multiple attempts to reach an enrollee before they are found to be non-compliant;
11) audit all user modifications to compliance or enrollee caseload history;
12) set the amount of time between call attempts;
13) provide manually initiated on demand outbound verification calls or alerts;
14) restrict manually initiated calls;
15) listen to voice verification files for each call;
16) provide quick view button for current calls as well as future scheduled calls;
17) cancel individual or multiple calls without adjusting the schedule;
18) provide proprietary multi verification channel registration and verification to reduce or eliminate voice failures;
19) require callbacks after verifications (Call forwarding spoofing);
20) set the number of call attempts prior to becoming non-compliant;
21) modify the compliance status of a call;
22) add user notes to a compliance call;
23) provide audited recordings of any user changes on the enrollee profile;
24) provide audit recordings of future call cancellations;
25) identify an inbound call by either caller ID or pin number (this is ideal in a case where more than one enrollee is using the same telephone number);
26) scheduling templates to minimize entering repetitive schedules;
27) avoid location spoofing;
28) easily filter curfew calls by a call number that is auto generated for each call;
29) filter curfew calls by compliance status;
30) filter curfew calls by date; and
31) filter calls by call type.

The present invention enables law enforcement to schedule inbound/outbound calls daily, weekly or monthly (recurs once every (x) number of days or weeks or months), or in a customizable schedule, and can include the following features (alone or in combination):

1) Randomly scheduled calls that allow the user to choose which days and the frequency of calls during a given weekly or monthly period;
2) customized frequency of required inbound/outbound calls;
3) enable or disable feature for inbound/outbound schedules;
4) ability to disable a schedule until a specific date;
5) open end date on curfew schedule so that the schedule recurs until the enrollee is disabled; and
6) ability to modify a curfew schedule.

The present invention can include a "Curfew Call: feature that can include any of the following aspects, alone or in combination:

1) designate the number of inbound/outbound calls to be placed to or from an enrollee during a specific period of time;
2) designate the number of alerts to be sent to an enrollee's smart device (for example, smart phone) requiring the enrollee to initiate an inbound call during a specific time frame;
3) random call frequency;
4) restrict inbound calls from unauthorized numbers or allow any phone number;
5) ability to identify an inbound call by either caller ID or a PIN number (this feature is used when more than one enrollee is using the same telephone);
6) schedule multiple attempts on outbound calls;
7) ability to set the amount of time between outbound call attempts;
8) ability to cancel individual or multiple calls without adjusting the call schedule;
9) ability to see scheduled outbound calls 30 days in advance;
10) manually initiated on demand outbound call;
11) quick view button capability to conveniently view outbound calls scheduled for the current day or for the next 30 days;
12) user ability to filter curfew calls for a specific enrollee by call number, date, compliance status, or call type;
13) call forwarding detection; and
14) alerts to the user if the enrollee fails to check in or check in outside of the required schedule time.

The present invention can include the following Additional Call Features:

1) proprietary multiple verification channel registration and verification to reduce or eliminate voice failures;
2) ability to listen to voice verification files for each call;
3) call review capabilities along with the ability to modify compliance and add notes to calls;
4) audit recordings of any user changes;
5) scheduling templates to avoid entering repetitive schedules;
6) restrictions placed on the smartphone app to prevent it from being deleted or tampered with
7) automated alert to the user if enrollee's smartphone device battery is low, has been turned off, or if the device is dead 8) agency feature that allows the enrollee to complete a verification call after a voice failure;
9) allows the enrollee to use more than one landline telephone number to be monitored on;
10) ability to cancel future scheduled inbound/outbound calls;
11) ability to export for compliance history reports;
12) ability to generate call history reports by specified date; and
13 ability to generate compliance activity reports per enrollee, per user, and per entity.

The following are benefits of the Outbound Curfew Management feature of the present invention:
1) increases productivity for the agency by automating verification of an enrollee's whereabouts without interaction from the user;
2) increases productivity by preventing false non-compliances due to schedule changing abilities, call review, and call compliance modification features;
3) increases productivity by preventing false non compliances by using call adjustment or cancellation features for scheduled or allowed time away from home;
4) provides user accountability by auditing all user changes and modifications to enrollee profiles;
5) provides a recording of each call for user review or proof of an imposter; and
6) aids users in combating location spoofing.

Location Services (LBS)

The present invention can include Location Based Services (LBS) which allows the user to verify a participant's whereabouts using multifactor location verification technology. The ShadoWatch can incorporate Wi-Fi, GPS, and Network location technology to increase location accuracy while enhancing battery life. The ShadoWatch can feature an attractive tamperproof wrist watch with color display. The watch can also be water-proof and include motion sensors, vibration alerts, messaging, heart rate and blood pressure detection. The watch can offer the ability to communicate with the participant by using two-way voice or electronic messaging. The watch also can have a QR activation feature that allows for a convenient and effortless activation process for users in the field. The ShadoWatch is preferably managed through the ShadowtrackONE™ total corrections platform designed for managing all services from one unified easy to use platform. LBS can also be paired with voice verification and facial recognition technology to positively identify the participant. Shadowtrack offers the flexibility of a minimally invasive tracking solution utilizing LBS on a landline telephone, mobile telephone or via the Shadowtrack mobile. This allows the participant to be discreetly monitored without having to wear any equipment.

The location services feature of the present invention allows the agency, such as a law enforcement agency, to:
1) efficiently monitor the whereabouts of an enrollee during a specific time frame;
2) efficiently monitor if the enrollee is attempting to enter a restricted area;
3) monitor an enrollee at a specific address or within the range of an entire state;
4) detect location spoofing; and
5) use on demand or automated random location frequency.

In one embodiment of the present invention, the location of the enrollee can be verified in the following ways, alone or in combination:
1) cellular triangulation of the smart device (for example, for the ShadoWatch);
2) GPS positioning coordinates;
3) scheduled silent location verification;
4) silent on demand user initiated location verification;
5) pairing location services with voice verification and/or facial recognition to ensure the enrollee is with the telephone device during location verification; and
6) on demand manual GPS location request.

In one embodiment of the present invention, when the verification call is completed, location coordinates are sent to the Shadowtrack® platform via an application protocol interface (API).

The user can review location results via the following ways:
1) displayed on a map via the enrollee's profile;
2) displayed on the enrollee compliance tab via a "View Map" button that is listed for each inbound or outbound call;
3) displayed with a color coded PIN for easy viewing: green for compliant (inside fence) and Red for non-compliant (outside fence);
4) GPS coordinate results logged on a map on the enrollee's compliance call details;
5) GPS results displayed with a color coded PIN on a map within the call details for easy viewing as Green for compliant (inside fence) and Red for non-compliant (outside fence); and
6) location verification results logged on the enrollee compliance tab via the mobile app.

Additional location verification features include:
1) compatibility with all major cellular carriers;
2) on demand voice verification combined with location verification;
3) option to initiate facial recognition verification in the event of a suspicious voice verification alert;
4) allows the user to create multiple Inclusion Zones to verify if the enrollee is at home, school, work, treatment program, etc.;
5) allows the user to create multiple Exclusion Zones to verify if the enrollee is near a restricted area;
6) customizable radius options to broaden or tighten a designated location area;
7) allows the user the option to set up a state radius in comparison to the enrollee's designated location address;
8) a feature set at the admin level that allows the agency to set all enrollee location radius's to a state wide parameter depending upon a certain interview protocol assigned to them;
9) an alert to the user if the enrollee does not initiate their location within a specified time frame;
10) API error for failure to reach the app due to the device being turned off or the app is not running
11) the ability for the Shadowtrack® platform to send messages that display an alert on the enrollee's smart device screen that must be manually dismissed;
12) feature that automatically prompts the enrollee on the next call to opt in to location services on their mobile device if an opt out occurs at any time;
13) mobile registration feature that alerts the user if a mobile phone number is "Not Locatable"; and
14) allows the user the ability to override location coordinates manually.

The following are some benefits of the location services feature of the present invention:
1) improves efficiency by allowing users to automate monitoring enrollee's whereabouts on a consistent basis;
2) non-compliant alerts to help the user manage enrollee non-compliance due to being outside of a designated location;

3) assists in combating enrollees attempting to turn off Location services on their device to prevent location verification by alerting the user when this happens;

4) prevents location spoofing; and 5) allows the user the ability to tighten the radius area to 5 miles but also broaden the radius area for the entire state of the enrollee's designated location address.

Self-Report Interview (SRI)

In one embodiment, the present invention includes a "self-reporting" service feature that consists of an interactive voice interview of customized questions that allows the user to obtain current information for the participant without the need for a face to face visit. The participant can conveniently complete their interview utilizing any telephone device or via the Shadowtrack mobile App. The SRI service supports any language and includes automatic transcription of participant responses. An exception report is generated from the participant responses and which the users can conveniently access. Exception responses are also noted on the participant profile via an audio file and can automatically be transcribed from speech to text. The SRI also includes scheduled reminders that can be placed to the participant via phone call, text, or email. Interview reminders improve participant compliance and ensure interview sessions are completed in a timely manner. The self-reporting service can be paired with LBS to not only verify the participant's whereabouts during the self-reporting session but to also randomly verify their location at any time during the month.

Utilizing the Interactive Voice Interview (Self-Report) service of the present invention allows the agency to:

1) improve efficiency by eliminating user contact directly with the enrollee to retrieve updated information ranging from enrollee contact information, employment status, interaction with law enforcement or arrests, or any other type of information the user would like to retrieve from the enrollee;

2) improve enrollee accountability by reminding the enrollee they have an upcoming self-report session; and 3) obtain current records and contact information for the enrollee in a more efficient manner.

In various embodiments of the present invention, the Interactive Voice Interview feature can include:

1) the ability to schedule the interview to begin on a specific date;

2) the ability to schedule the interview duration to be an hour, day, week, month; and 3) option to schedule the interview to recur daily, weekly, monthly, and yearly.

In various embodiments of the present invention, interview reminders of the Self-Report service can be scheduled in the following ways:

1) a certain number of days prior to the interview period;

2) hours or minutes prior to interview expiration date;

3) recur every day until the end of the interview period;

4) recur a fixed number of times; and 5) logic that stops interview reminders once an interview has been complete.

In various embodiments of the present invention, features of the Self-Report service can include:

a) supports any language as well as hearing impaired;

b) interactive voice response that allows the enrollee to respond to questions asked during self-reporting;

c) recordings (such as way file) of all enrollee interview responses the user can hear;

d) ability to create custom self-reporting protocols with an unlimited number of questions;

e) option to accept self-reporting interviews after the interview period has expired;

f) allows you to pair random location verification called "Quick Checks" with self-reporting;

g) agency feature that allows the enrollee to complete an interview after a voice verification failure;

h) allows the user to create interview schedule templates per Entity to avoid repetitive entering of schedules;

i) administrative ability to lock Interview schedule templates to prevent users from modifying templates;

j) allows the user the ability to share Interview schedule templates with additional sub entities;

k) ability to require an Interview to be completed by forcing the enrollee to complete the interview on the next inbound or outbound call once the interview period has expired;

l) when a verification call API request is received, an alert will be displayed on the screen, along with a sound and vibrate, requesting that the enrollee call in to the Shadowtrack® platform to complete their interview by clicking on the alert window. The alert cannot be dismissed and prevents use of the mobile device until the enrollee initiates the call or manually dismissed the alert;

m) when the verification call is completed the interview questions will be played as well as the location coordinates are sent to the Shadowtrack® platform via API. This can be set to automatically be sent out within minutes of the call. Shadowtrack® has logic to set off an alert if the location coordinates are not received by the user within five minutes; and n) allows the option for the enrollee to initiate facial recognition after an alert is received on the smartphone. Once identity verification is completed the enrollee will receive an SMS text of the interview questions. The enrollee can respond to the interview questions via text message or voice.

The following are some benefits of the Interactive Voice Verification feature of the present invention:

1) Increases productivity for the agency by eliminating the user's personal interaction to obtain information from the enrollee;

2) Allows the agency to designate how frequently self-reporting is required in order to aid in upkeeping of current information for the enrollee;

3) Implements enrollee responsibility in reporting updated information to the user by placing self-reporting reminders;

4) Increases user efficiency by sending automated reports for enrollee's that fail to self-report;

5) Allows the user to pair random location verification with self-reporting to ensure the enrollee has not left a designated area during a self-reporting period; and 6) No transcription is required with smartphone.

Notifications

An embodiment of the notification service of the present invention provides a robust automated solution to communicate with the participant. This service allows the user the flexibility of sending notifications in several different formats including Text Message, Text to Speech (TTS), Email, and Voicemail. The user can schedule one time or recurring messages to one participant or multiple participants at the same time. The Shadowtrack application logs the date and time the participant received the notification, the details and format of the message, and the date and time the participant listened to the message. Future scheduled notifications can be cancelled at the user's discretion. This service allows the user to view all notification history for a participant as well as view future scheduled notifications for a period of time, for example, up to ninety days (90) in advance.

In a preferred embodiment, utilizing the Notification service allows the agency to:

1) Improve efficiency by eliminating user contact directly with the enrollee;
2) Improve efficiency by allowing the user to send a notification to multiple enrollees at one time;
3) Scheduled and random customized notifications via speech, text to speech, text messaging or uploaded recorded voice, for example, which is useful for court and probation appointment reminders; and
4) Conveniently schedule exclusion dates for notifications so that notifications are not placed on specified dates.

Notifications Platform Functionality

1) Schedule notification in the following ways, for example:
 a) Email;
 b) Text to speech with voice verification;
 c) Text to speech without voice verification;
 d) SMS;
 e) Voicemail; and
 f) Text to speech paired with SMS.
2) Example notification features:
 a) Ability to send out a mass notification to more than one enrollee;
 b) Ability to send more than one type of notification to an enrollee at a time;
 c) Ability to schedule a notification to occur at a specific time and date;
 d) Ability to schedule a notification to recur on a set schedule such as a daily, weekly, or monthly period;
 e) Ability to schedule exclusion dates for a notification so that notification are not placed on specified dates
 f) Ability to schedule a notification to recur randomly during a daily, weekly, monthly, or random period;
 g) Ability to verify if a notification message was heard by an enrollee;
 h) Ability to select "Voice Verification" so that the enrollee must verify their identity before the notification message plays;
 i) Phone call placed to the enrollee that allows the enrollee to listen to the notification message;
 j) Allows the enrollee to call into the application in the event of a missed call and hear the notification message;
 k) Ability to turn voice verification off for notifications;
 l) Ability to make additional attempts to deliver the notification if a voice failure occurs;
 m) Ability to verify the date and time an SMS or other notification was sent to the enrollee;
 n) Ability to pair voice verification with text to speech and voicemail notifications during additional attempts to deliver the notification message;
 o) Ability to restrict notifications by enrollee;
 p) Allows the enrollee to send a voicemail to their assigned user;
 q) Support for multiple languages, including Spanish and English, text to speech technology converting typed phrases to voice;
 r) Push notification sent to the enrollee via their mobile device that allows them to view the notification message on their mobile device; and
 s) Ability to conveniently schedule notifications per enrollee and per entity from the User's main dashboard.

Example Benefits of Notifications

1) Increases productivity for the agency by eliminating the user's personal interaction to communicate messages;
2) Increases productivity by allowing the user to deliver messages to multiple enrollee's one or more times; and
3) Increases efficiency by allowing the user to verify the enrollee has received the notification message.

Random Drug Testing (RDT)

A preferred embodiment of the drug testing service of the present invention offers a turnkey-solution to refine the entire drug testing process from start to finish. Shadowtrack's Random Drug Test is a solution for all aspects of drug testing including automated notification to the participant when they are selected to report for a test, an offender pay option (OPO) to collect payment for testing, and integration with testing facilities that allows for final test results to be documented in the application. Shadowtrack's approach to drug testing allows the participant to receive a notification to report for testing instead of requiring them to call into an automated system on a daily basis. This amounts to pointless additional calls and wasted officer resources. Users can create random or scheduled drug testing templates to designate the frequency of testing and include a custom notification message. Notifications can be placed to the participant via email, text to speech, or text. Shadowtrack's detailed color code reports allow the user to conveniently manage who is reporting for testing. The color code report can be viewed in a list, calendar, or graph format and can be exported in Excel or PDF format. Users can also view future scheduled notifications up to three months in advance. This allows the agency to properly plan staffing needs as well as office closures. Drug testing templates can conveniently be placed on hold or disabled. The RDT service also allows the user to designate specific dates they would like to exclude from scheduling drug testing notifications. This service improves the overall efficiency and productivity of users by automating the entire drug testing process.

Utilizing the Random Drug Test service allows the agency to accomplish the non-exhaustive list of tasks:

1) Allows the user to place enrollees into named groups for random or fixed scheduled drug testing notifications;
2) Have unlimited number of groups;
3) Allows the user the flexibility of suspending drug testing notifications at the agency's discretion;
4) Allows the agency the ability to modify notification templates;
5) Allows the user the option to move an enrollee to another group;
6) Custom report available to the user so they are aware of what enrollees have been notified to report for drug testing and/or have upcoming drug testing notifications scheduled;
7) Improve efficiency by automating drug testing notifications to enrollees only when a drug test is required;
8) Includes voice verification to ensure the correct person is receiving the drug testing notification message;
9) Includes the ability to send an SMS message once it is determined an enrollee has not answered the call;
10) Allows the enrollee to call into the Shadowtrack® system to hear the notification message if they miss the phone call;
11) Sends the agency analytical data via reports regarding drug testing results; and
12) Sends an alert to the enrollee via the smartphone app to view the drug testing notification message. The alert message must be initiated or dismissed.

Example Random Drug Testing Platform Functionality

1) Send Drug Testing notifications to an enrollee in one or more of the following formats:
 a) Voice without voice biometric verification;

b) Voice with voice biometric verification;
c) Text-to-Speech (TTS);
d) SMS (text messages);
e) Uploaded way file in any language; and
f) Text-to-Speech and SMS combined simultaneously.

2) Send "Drug Testing" notifications at the following frequencies:
a) Daily fixed schedule;
b) Weekly fixed schedule;
c) Monthly fixed schedule;
d) Daily random schedule;
e) Weekly random schedule;
f) Monthly random schedule;
g) Selectable applicable days that allows the user to exclude specific days of the week;
h) Allows the user to specify preferred times of the day to deliver drug testing notification message; and
i) Feature that allows the user to exclude drug testing days for their agency via a calendar so that drug testing notifications are not placed on these dates.

3) Multiple attempts to deliver a drug testing notification:
a) Shadowtrack® will automatically place additional retries to deliver a drug testing notification in the event of a missed call due to a no answer, hang up, voicemail, or answering machine;
b) Allows the enrollee to call into the Shadowtrack® application to hear a missed drug testing notification; and
c) The user can pair an SMS message to be sent to an enrollee's mobile if the enrollee does not answer the call attempts to deliver the drug testing notification message.

4) Create Custom drug testing templates:
a) Allows the user to create a custom template for each group that specifies drug testing frequency and custom drug testing message details;
b) Allows the user the ability to modify drug testing templates;
c) Allows the user the flexibility of suspending/unsuspending drug testing templates at the agencies discretion; and
d) Allows the user the ability to schedule specific holidays to restrict drug testing notifications from being sent out per entity.

5) The ability to place an enrollee into a group to designate drug testing frequency:
a) Allows the user to assign an enrollee to a group to automatically schedule the frequency of drug testing notifications;
b) Allows unlimited number of groups per agency; and
c) Allows the user the option to move an enrollee to another group to increase or decrease the frequency of drug testing notifications.

6) Reporting:
a) Custom reports available to the user so they are aware of what enrollees have been notified to report for drug testing and/or have upcoming drug testing notifications scheduled;
b) Report displays the time and date the enrollee received the drug testing notification;
c) Report displays the call disposition of the drug testing notification call;
d) Report displays the group name each enrollee is assigned to;
e) Report displays the enrollee's assigned user; and
f) Random Drug Test summary reports include the total number of enrollees utilizing the drug testing service, a breakdown of how many enrollees are in each group, and a breakdown of call results per enrollee.

7) Service Types:
a) Service can be used as a standalone or paired with any other Shadowtrack® service, for example.

Example Benefits of Random Drug Testing Service
1) Increases productivity for the agency by eliminating the user's interaction to notify an enrollee to report for drug testing;
2) Allows the agency to determine the days and times that are most convenient for enrollees to report for drug testing;
3) Allows the agency to place drug testing on hold for holidays or specific dates;
4) Allows the agency to set the discretion of how many enrollees report for drug testing; and
5) Provides the agency with analytical data as a way to document drug testing results in an effort to increase or decrease drug testing frequency for the enrollee or perform caseload studies.

Sobriety

A preferred embodiment of the present invention may include a sobriety module that works in conjunction the Shadowtrack mobile app. The app and device work with Android and IOS devices. In certain embodiments, BACtrack is an electronic device that is integrated with the Shadowtrack mobile app to utilize facial recognition, alcohol consumption detection, and location verification. The device requires no installation and can be purchased directly by the participant. Shadowtrack will send random alerts notifying the participant an "Alcohol Test is Required". Once the alert is sent, the participant will have a configurable amount of time to complete the Sobriety test before becoming non-compliant. Once the test is completed, the Blood Alcohol Content (BAC) score, location of the test, and a picture of the participant while performing the test will be logged in the participant's profile in the Shadowtrack application. If the initial BAC score is above 0.0 a secondary test will be initiated to verify the validity of the initial result. The Shadowtrack mobile app works in conjunction with the BACtrack device to detect spoofing with other devices and includes liveness testing to ensure the validity of each test. This service provides a discreet and cost-effective approach to sobriety testing.

If the test is completed, the device application may send the following results, for example, to the Shadowtrack® platform:
1) Blood alcohol score (BAC);
2) Location of the test; and
3) Picture of the enrollee.

Utilizing the Breathalyzer Option allows the agency to have the following features, for example:
1) Combine facial recognition with alcohol consumption detection via an electronic device that requires no installation and is purchased and shipped directly to the enrollee;
2) Facial recognition liveness test to prevent enrollees from using a photograph or recorded video;
3) Anti-spoofing that includes the ability to detect other devices within Bluetooth range throughout the duration of the sobriety test;
4) Ability to detect the blue light on the breathalyzer device is on during a sobriety test to prevent spoofing; and
5) Outbound voice verification request only (Independent of alcohol test).

Example Breathalyzer Platform Functionality:
1) Combines facial recognition with alcohol consumption detection via an electronic device, such as BACtrack that requires no installation and is purchased and shipped directly to the enrollee. In a preferred embodiment, when the Shadowtrack® app receives a verification call API request, a push notification will be displayed on the screen, along with a sound and vibrate, requesting that the enrollee call into the Shadowtrack® platform to complete a sobriety test. The alert will stay on the display until the enrollee initiates the call or manually dismisses the alert; preferably, the BAC value is transmitted to the first monitoring entity by a REST API call from the BACtrack® device which requests and receives responses via HTTP protocol (a REST API defines a set of functions which developers can perform requests and receive responses via HTTP protocol such as GET and POST").

2) Enrollee may be prompted to place their face inside a designated square area on their mobile device to ensure accuracy of facial recognition during enrollment and subsequent sobriety testing;

3) When the verification call is completed, location coordinates may be sent to the Shadowtrack® platform. This can be set to automatically send out within a set time, such as 20 minutes of the call. In one embodiment, Shadowtrack® has logic to set off an alert if we do not receive the location coordinates within five minutes;
   a) Inbound voice verification request (Independent of alcohol test);
   b) There may be a button on the app that generates a phone call to the Shadowtrack® platform to perform a voice verification; and
   c) Once this button is pressed, the app may also send location coordinates.

4) Alert message displayed to the enrollee when low battery of the breathalyzer device is detected.

5) Facial recognition liveness test to prevent enrollees from using a photograph or recorded video.

6) Anti-spoofing that includes the ability to detect other devices within Bluetooth range.

7) The Shadowtrack® platform may trigger a non-compliant event and notify the assigned user for any of the following reasons, for example:
   a) The breathalyzer score is greater than a predetermined level;
   b) Failure to receive a reading from the device within time specified;
   c) Picture does not match enrollment picture in the Shadowtrack® application. NOTE: An event can be manually converted to non-compliant and the user will be required to add notes as to why the status was changed;
   d) An alert may be sent to the user if a test result is not received within a predetermined time frame; and
   e) Error for failure to reach the app due to the device being turned off or the app is not running.

8) Send random "Sobriety Test" notifications in one or more of the following non-exhaustive list of formats:
   a) Voice without verification;
   b) Voice with voice biometric verification;
   c) SMS;
   d) Text-to-speech (TTS);
   e) Uploaded WAV file in any language; and
   f) Alerts via the Shadowtrack® Mobile App.

9) Attempts:
   a) Single or Multiple test attempts prior to non-compliant; and
   b) Adjustable time frame between attempts.

10) Perform location validation:
   a) Perform silent location verification checks utilizing GPS during Sobriety tests; and
   b) User ability to send an alert to the enrollee for live video interaction in the event of a failed Sobriety test.

11) User non-compliant notification types:
   a) Bridge voice call with enrollee and user;
   b) SMS;
   c) TTS; and
   d) WAV.

12) Reporting:
   a) Detailed compliance report to include:
      Date and time of test
      Location of test
      BAC Score
      Picture
   b) Facial recognition score—facial recognition technology may be used to compare the image taken during the test with the reference image obtained during enrollment. We will then use the confidence score received against a facial mismatch threshold established in the Shadowtrack® application.
      In addition to all other data provided on the Shadowtrack® platform
   c) Reporting methods:
      Instant upon non-compliant event
      Summary on a specified time table 13) Service Types:
   a) Sobriety tests can be a stand-alone service or incorporated with any of the other Shadowtrack® platform services.

14) Unscheduled Tests:
   a) If a test is received outside of a scheduled screening window, the test is considered a non-compliant event and shall be indicated as "Outside Window" under the compliance heading "Test Window"; and
   b) Tests results received within the time allotted shall be labeled "Inside Window".

Benefits Include:

1) Economical—service will be provided with little to no markup on existing Shadowtrack® services;

2) Ownership—enrollee owns device and can continue testing after completing court ordered program to aid in maintaining sobriety;

3) Easy to use—takes less than one minute to perform screening;

4) Unobtrusive—no embarrassing leg devices that can affect employment, family life or interfere with medical conditions;

5) Convenient—small device—can be carried in your pocket; and

6) Unified platform—Integrated with all other Shadowtrack® solutions.

Caseload Management (CLM)

In a preferred embodiment, the Caseload Management service of the present invention allow the user to manage an enrollee's case while on the Shadowtrack® program.

Shadowtrack's caseload management (CLM) service provides an all-inclusive solution for users to manage their caseload more efficiently. CLM can be paired with any of Shadowtrack's other services or integrated with the agencies' existing case load management system. Users can take advantage of the CLM service by utilizing automated reminders triggered by requirement deadlines and create custom reminders and tasks that help the user and participant to stay on top of required duties. Users can also utilize the caseload calendar that allows for scheduling of appointments as well as an overall view of the participants upcoming scheduled events. The CLM service allows an agency to utilize custom mail merge documents, upload documents, attach them to the participant profile, enter free handed notes, and keep track of analytical data and demographics for participants. Shadowtrack's custom caseload reports can provide an agency with overall analytical data as a way to document demographics, crime statistics, and success/failure rates to perform caseload management studies.

Caseload Management Service Allows the Agency to:
1) Integrate with all of Shadowtrack®'s modules to increase user efficiency;
2) Improve enrollee accountability by reminding the enrollee they have an upcoming deadline;
3) Obtain current records and contact information for the enrollee in a more efficient manner; and
4) Send scheduled and random customized notifications via text to speech, text messaging, email, or uploaded voicemail. Great for court and probation appointment reminders Example of Caseload Management Platform Functionality
1) Customizable API integration capability with 3rd party software;
   a) Import data into the Shadowtrack® application that can include but is not limited to the following:
      Name
      Address
      Phone number
      Color Code
      Entity referral code
2) Conditions
   a) Conditions are customizable per entity and can be setup up based on the individual needs of the entity;
   b) Auto populated deadline reminders for conditions can be generated for the enrollee to improve efficiency in completing court ordered requirements; and
   c) Ability to override any automatic notifications.
3) Caseload Management Events
   a) "Requirements by Offense" button that generates a list of requirements that are based on the enrollee's offense;
   b) Scheduled reminders sent to the enrollee based off of requirement deadlines designated by the user;
   c) Shows the auto populated dates set by each requirement the enrollee is scheduled to complete;
   d) Allows the user to enter dates for program deadlines, enrollment dates, payment dates, and completion dates;
   e) Allows the user to print a checklist that lists all condition requirements, deadlines, and Caseload Management information entered by the assigned user;
   f) Ability to automatically notify enrollee a fixed number of days prior to completing the program of the date the program will end;
   g) Ability to send scheduled TTS, SMS, and email notifications to the enrollee;
   h) Option to send a text message to the user when an interview (Self-Report) is incomplete;
   i) Logic that prevents editing of Caseload Management Notifications that have already been sent;
   j) The ability to view time and date confirmation on the dashboard indicating that the enrollee received their reminder alert;
   k) The enrollee profile will be automatically assigned a color to alert the user of the status of completing requirements. The requirement stages are color coded as follows:
      GREEN—Requirement is in good standing
      YELLOW—Requirement approaching deadline
      ORANGE—Requirement in "Grace Period"
      RED—Requirement passed
      BLUE—Requirement is complete
   l) A report will be available to the entity so they can review the color code status of each enrollee.
4) Calendar
   a) An event calendar per enrollee that displays all future deadline and condition requirements for the next 30 days;
   b) Ability to schedule appointments via the calendar;
   c) Ability to send out an appointment reminder via email one day prior to the appointment date;
   d) The enrollee calendar will also display conditions and requirements as follows:
      Condition due dates
      Condition reminders
      Appointments
      No show
      Drug test notification
      Ability to see each requirement in the stage color
      Ability to add manually caseload event
5) Notes
   a) Case notes can be entered by users along with an audit trail so the user name that entered the note is listed
6) Automated Mail Merge Letters
   a) Automated certificate of completion letter generated by the application once condition requirements have been successfully completed;
   b) Ability to generate a "Terms and Condition" form with all program requirements merged on the document;
   c) Transactions;
   d) Ability to add debits and credits;
   e) Ability to view transactions by type;
   f) Show up to date balance on account;
   g) Ability to send payment reminders based on payment due date; and
   h) Auto generated transaction ID numbers.
7) Reports
   a) Recidivism reports that allow the entity to run annual reports on enrollees that have completed program requirements if the enrollee has been rearrested;
   b) Customizable reports per entity that can display the following:
      Misdemeanor referrals
      Felony referrals
      DWI referrals
      DWI with required meetings
      Automatic referrals
      Number of enrollments
      Number of appointments
      Reports with statistical data showing the following:
      Profile demographics
      Charges
      Program conditions and stage requirements
      Completed total enrollees
      Success rate
      enrollee compliance
8) Documents
   a) Ability to upload and store documents, certificate, and test results
9) Contacts
   a) The ability to associate authorized contacts with the enrollee;
   b) The ability to associate multiple contact types to an enrollee such as Caseworker, Judge, Lawyer, family member, etc.; and
   c) The ability to identify contacts as "Share Authorized" indicating the user has permission to share information regarding the enrollee with this contact.
10) Authorized Lab a) The ability to associate an enrollee with an authorized lab location for drug testing; and
b) The ability to generate an automated mail merge letter to be sent to the authorized lab notifying them of enrollee information, lab requirements for testing, and that the enrollee is going to be reporting for drug testing on a specific date.

Benefits of Caseload Management

1) Provides user accountability by auditing all user changes and modifications to enrollee profiles;
2) Improves efficiency by allowing users to automate program condition deadlines and reminders to the enrollee;
3) Increases efficiency in user Caseload Management by sending automated reports to users for enrollee's that fail to meet program deadlines;
4) Increases productivity by allowing the user to deliver messages to multiple enrollee's one or more times;
5) Allows the agency to determine the days and times that are most convenient for enrollees to report for testing, counseling, or face to face meetings;
6) Provides the agency with analytical data as a way to document demographics, crime stats, success/failure rate or perform Caseload Management studies;
7) Economical—service will be provided with little to no markup on existing Shadowtrack® services; and
8) Calendar feature to easily manage an enrollee's upcoming appointments, court dates, etc.

Example Mobile Application

A preferred embodiment of the "Shadowtrack®" mobile app provides the ability to monitor an enrollee using voice or facial recognition for curfew, self-reporting, location verification, and sobriety via their mobile device. The mobile app features on demand push notifications for sobriety, self-reporting, curfew, and location verification, for example.

The Mobile Application May Allow the Agency to:

1) Conveniently complete a voice enrollment via the mobile app;
2) Conveniently Initiate on demand or scheduled push notifications to the enrollee;
3) Improve enrollee compliance by having them call into the application to complete a push notification rather than having random phone calls being placed to the enrollee;
4) Improve the accuracy of location verification via the mobile app;
5) Combat enrollee spoofing of their mobile device with built in technology to detect this; and
6) Monitor movement of the enrollee mobile device during lengthy periods of inactivity in the event the user suspects the enrollee is not with their mobile phone.

Example Mobile Application Platform Functionality

1) Mobile App

Available for Android and iOS users
Available in English and Spanish
Scheduled and on demand push notifications to the enrollee via the mobile app for location verification, interview, voice verification, and sobriety
Automated notification sent to the user if the enrollee fails to initiate a push notification by a specific time frame
Alert to the user if the enrollee logs out of the mobile app at any time
Alert to the user if the enrollee denies permission to receive notifications. If the enrollee turns off notifications at any time while utilizing the mobile app a non-compliant "Permission Denied" call will be listed on the compliance tab.
Allows completion of sobriety push notifications during curfew outbound calls
Improves enrollee compliance by placing multiple attempts to reach the enrollee by SMS and phone when a push notification is not responded to
Motion detection technology so the user can monitor suspicious time periods of enrollee inactivity with the mobile phone
Ability to obtain mobile device information like device model and version when an enrollee logs into the mobile app
Noncompliance message displayed to enrollee that states the assigned user will be notified when they log out of the mobile app
Silent Location verification performed when an enrollee logs out of the mobile app
When the app receives a verification call API request, an alert will be displayed on the screen, along with a sound and vibrate, requesting that the enrollee call into the Shadowtrack® platform by clicking on the alert window. The alert cannot be dismissed and prevents use of the mobile device until the enrollee initiates the call or manually dismisses the alert
Ability for enrollee to perform a voice verification request via the telephony network and the option to perform a verification request using a Wi-Fi data network.

2) Facial Recognition

Requires the enrollee to take a picture of themselves upon enrollment to ensure facial recognition accuracy;
Pairs facial recognition with Sobriety to ensure the identity of the enrollee when completing a sobriety test
Automated facial recognition triggered when a failed voice verification occurs
Ability to send a request for live video interaction between the user and the enrollee in the event of a failed facial recognition
An SMS message is sent to the enrollee once a push notification expires and the enrollee has not responded
An auto generated phone call is placed to the enrollee once a push notification expires and the SMS message has already been sent out and the enrollee still has not responded
The facial recognition threshold allows the user to easily raise or lower the enrollee facial recognition score.
Facial recognition threshold can be set at a preferred score per entity or per enrollee
Enrollee is prompted to place their face inside a designated square area on their mobile device to ensure accuracy of facial recognition during enrollment and subsequent facial recognition push notifications 3) Benefits of the Mobile Application 1) Improves user efficiency by preventing so many non-compliant alerts since the enrollee is calling in to report instead of receiving random calls'
2) Improves enrollee accountability by attempting to reach the enrollee in the event of a failure to respond to a push notification;
3) Improves location accuracy by obtaining location coordinates for the enrollee directly from the mobile app utilizing GPS;
4) Provides additional security by featuring built in technology to prevent location spoofing; and
5) Automated non-compliance alerts sent to the user when an enrollee logs out or deletes the mobile app.

Officer Mobile App (OMA)

The Officer Mobile App (OMA) allows the user to easily access and manage their caseload via their mobile device.

The OMA allows the user to view a custom caseload summary of participants per service. User can also access compliance notifications, view tracking history, initiate on demand or scheduled verification sessions, and initiate on demand or scheduled location-based services. In addition to this, the user can send custom notifications and initiate two-way communication to the ShadoWatch™. The OMA provides a practical solution to manage one's caseload both in the office and in the field. With the user App coupled with the ShadoWatch™, the user is always in contact with the participant.

The Officer Mobile Application Allows the Agency to:
1) Increase efficiency by allowing the officer the convenience of managing their caseload via their mobile device;
2) Increase enrollee compliance by allowing the user the ability to prompt a live interactive video session or phone call to the enrollee in the event of a non-compliance event;
3) Allows the user to specify custom viewing of enrollee compliance history; and
4) Increase efficiency by sending on demand or scheduled custom push notifications to the enrollee via their mobile phone.

Example Officer Mobile Application Platform Functionality
1) Available for multiple platforms, such as Android and iOS users;
2) Can be used with a mobile device, such as a phone or tablet;
3) On demand buttons to initiate requests or view compliance;
4) Allows the user to create scheduled and on demand push notifications to their enrollees for location verification, interview, voice verification, and sobriety;
5) Custom compliance viewing history capability that allows the user to choose viewing options for a set number of days, weeks, months, or a custom date period;
6) Allows the user to initiate on demand phone calls or live video interactive sessions;
7) Allows the user the convenience of listening to calls that result in a failed voice verification by playing the way file from the call on their mobile device;
8) Allows the user to initiate on demand location verification of the enrollee;
9) Customizable compliance alert frequency that allows the user to designate how often they would like to receive compliance alerts such as instantly, daily, or weekly; and
10) Customizable administrative option for viewing permissions that restrict the user from viewing other user caseloads or entities if required.

Benefits of the Officer Mobile Application
1) Improves user efficiency and mobility by allowing the user to effectively monitor their caseload via their mobile device;
2) Improves enrollee compliance by allowing the officer to initiate on demand phone calls and live video interaction in the event of a non-compliance; and
3) Improves user efficiency by allowing the user to complete enrollments, make adjustments to schedules, and review compliance all from their mobile device.

Example Travel Pass
The travel pass feature allows for efficient and concise management of participants returning home from approved travel. This service works in conjunction with Shadowtrack's caller ID, voice verification, and location verification services. The service allows the user to enter "Return Dates" for the participant. The participant is then required to check into Shadowtrack's automated system by this date. If the participant fails to check in by this date, fails verification, or is found to be outside of the designated location, they will be considered non-compliant. An automated email will then be sent to the user. The travel pass feature increases participant's accountability and ensures the user is effectively managing the participant's whereabouts while on supervision.

The travel pass service allows the agency to:
1) Efficiently manage caseload travel requests via the application eliminating direct contact with the enrollee to verify they have returned from travel;
2) The automated non-compliance alert allows the user to enforce enrollee accountability to return from travel by required return dates;
3) Minimize the risk of a user forgetting about a travel pass request;
4) Verify the enrollee is back at their required location using location services; and
5) Gives the user the ability to schedule travel passes via the User Mobile Application.

Example Travel Pass Platform Functionality
1) Custom Shadowtrack script that allows the enrollee the option to check in from travel. The script may play as follows:
   "To notify your user that you have returned from travel, press 5"
   Once 5 is pressed, we verify that the location is within the authorized radius
2) Ability to enable the "Return From Travel Check In" custom script only when a "Travel Pass Start Date" is entered in the application otherwise the custom script will not play;
3) A travel pass section listed at the top of the compliance tab to enter the travel "Start Date" and "Return Date";
4) Travel pass results logged on the compliance tab;
5) A non-compliant call logged once the "Return Date" has arrived and the enrollee has not checked in;
6) The ability to generate a report to view what enrollees have not completed a check in by the required "Return Date"; and
7) Ability to run the following reports during a specified time period:
   Total travel passes requested
   Total travel pass returns
   Total unreturned travel passes
   Total travel passes returned inside fence
   Total travel passes returned outside fence Benefits of the Travel Pass Service
1) Eliminates direct contact between the enrollee and user;
2) Automates enrollee check in from travel;
3) Increases enrollee accountability by automatically obtaining location information when the enrollee checks in; and
4) Allows the user to efficiently manage and monitor travel passes by reviewing the travel pass reports.

12. TETHER

The Tether device may be paired with the Shadowtrack® mobile app via Bluetooth, for example. In the event that Bluetooth is disconnected, a verification call is prompted to ensure the enrollee is with their mobile device and verify Bluetooth connection with the Tether device is re-established. A non-compliance notification will be sent to the user if Bluetooth signal is lost or there is any attempt to tamper with or cut the Tether device strap. The user will also be notified when a signal from the Tether device is not received within a given a period of time or the enrollee is found to be outside of the designated monitoring area 12.1 the Tether Allows the Agency to:
A. Verify the enrollee has their mobile phone and Bluetooth is connected with the Tether device via a verification call when a Bluetooth disconnection alert is received
B. Confirm the Tether device Bluetooth is re connected to the enrollee mobile device
C. Combat possible enrollee removal or tamper of the device by sending an alert to the user when a signal from the device is not received within a given period of time
D. Confirm the enrollee is at the required monitoring location
E. Improve efficiency with detection of a Tether device low battery and detection of a low battery on the enrollee mobile telephone 12.2 Tether Platform Functionality
A. Pairs with any mobile device that has Bluetooth capability
B. Incorporates voice verification and live video interaction in the event of a non-compliance alert
C. Detection of Bluetooth disconnection or inactivity during a specified period of time
D. Detection of Tether device tampering
E. Ability to review Tether compliance for the enrollee via the Shadowtrack® application and the user mobile app
F. Ability to print and export compliance history
G. Location verification performed continuously
H. Alert to the user if enrollee is found to be outside of a designated area
I. Sends an alert to the user when the Tether device battery is low
J. Allows the user to send an alert to the enrollee when low battery of their mobile phone is detected 12.3 Benefits of the Tether Device
Prevents false non-compliance by allowing the user to initiate a voice verification or live video request in the event of a non-compliance
Ensure enrollee accountability by verifying the Bluetooth on the Tether device is connected
Allows the user to be proactive by sending out alerts when a low battery on the Tether or mobile device is detected 13. Additional Application Services
A. Import data management
B. Import data via Excel file
C. Application protocol interface (API)
D. Much faster and efficient than previous versions
E. Universal "Google-like" quick search capabilities to search for users by name, enrollee by name, telephone number, call number, ID number, and by entity name
F. Spanish and English Text-to-speech technology converts typed phrases to voice
G. Ability to assign multiple Users to one enrollee
H. Ability to move a User to a different Entity
I. Ability to move a User's entire caseload
J. Automatic password expiration feature for users. The feature allows the agency to require a password reset for each user upon their first login and every (x) number of days
K. Customizable compliance tab option for users so they can filter by compliance data they prefer to see
L. Customizable entity settings User IP Address tracking that includes the following, date and time of each login, IP Address, User agent string, Browser, and Browser version Surety Shadowtrack® Surety Management Service (SMS) provides an electronic solution to surety companies for managing the powers they guarantee for their agencies. The SMS service allows surety companies to easily import their inventory of powers in the Shadowtrack® application. The surety company can assign those powers to various agencies, and then continue to track the progress of those powers once they have been assigned. Surety companies can also utilize this service to document and manage licenses, appointments, and contracts per agency. The SMS service includes detailed settlement reports that aid the surety company in keeping track of agency balances as well as all other aspects of surety management.

Bail

Shadowtrack® Bail management service (BMS) allows bail companies to manage their bonds and defendants. This service allows bond companies to work in conjunction with the surety company if desired. This service can also be paired with Shadowtrack® other monitoring services including location verification using the ShadoWatch™ or mobile App, custom notifications, and Shadowtrack® participant pay solution. Bail companies can execute powers, enter detailed court information, assign bonds to agents, and keep track of defendant balances.

Watch/Bracelet

Figure 2:
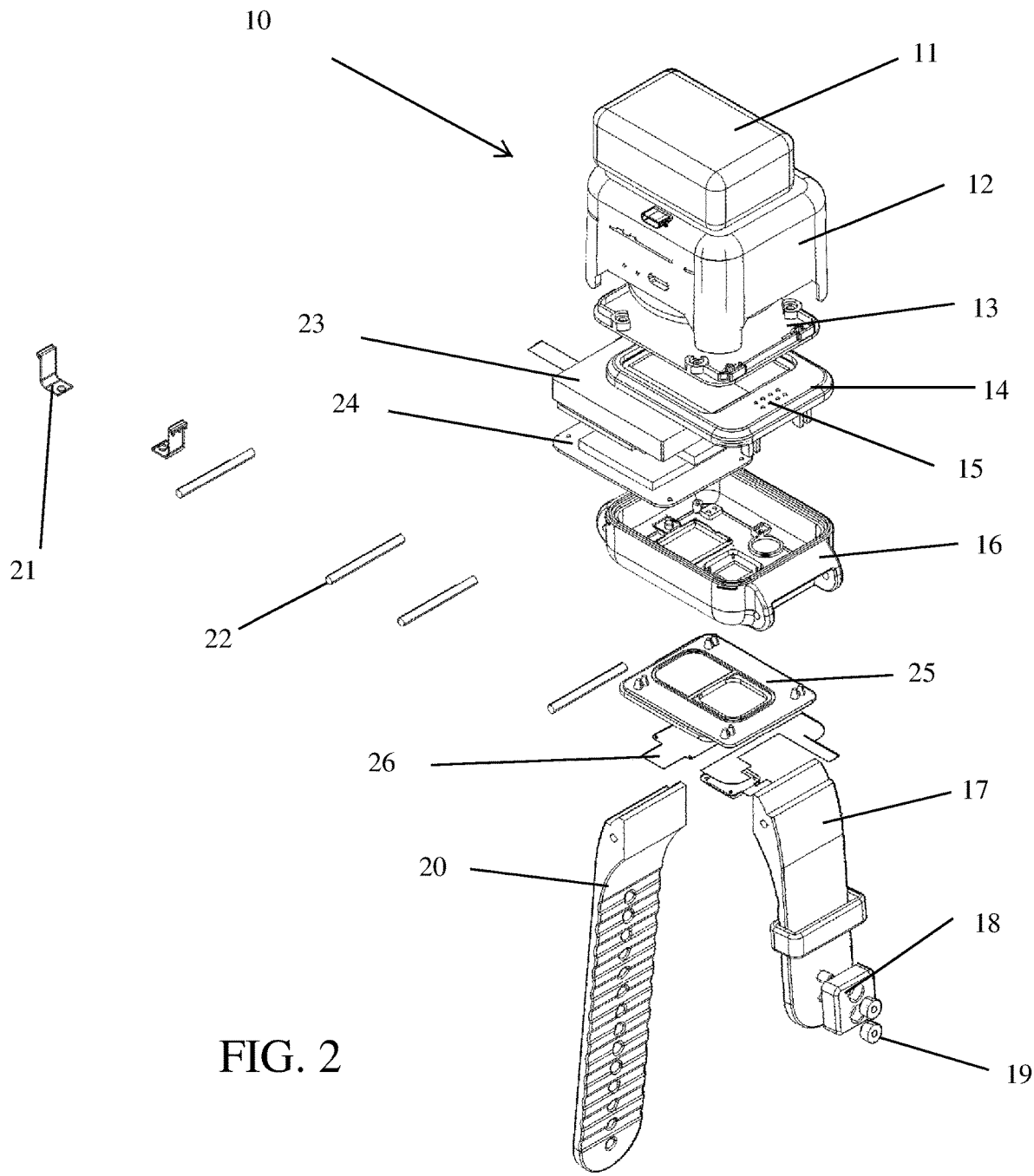
FIG. 2 is an exploded view of FIG. 1.
Figure 3:
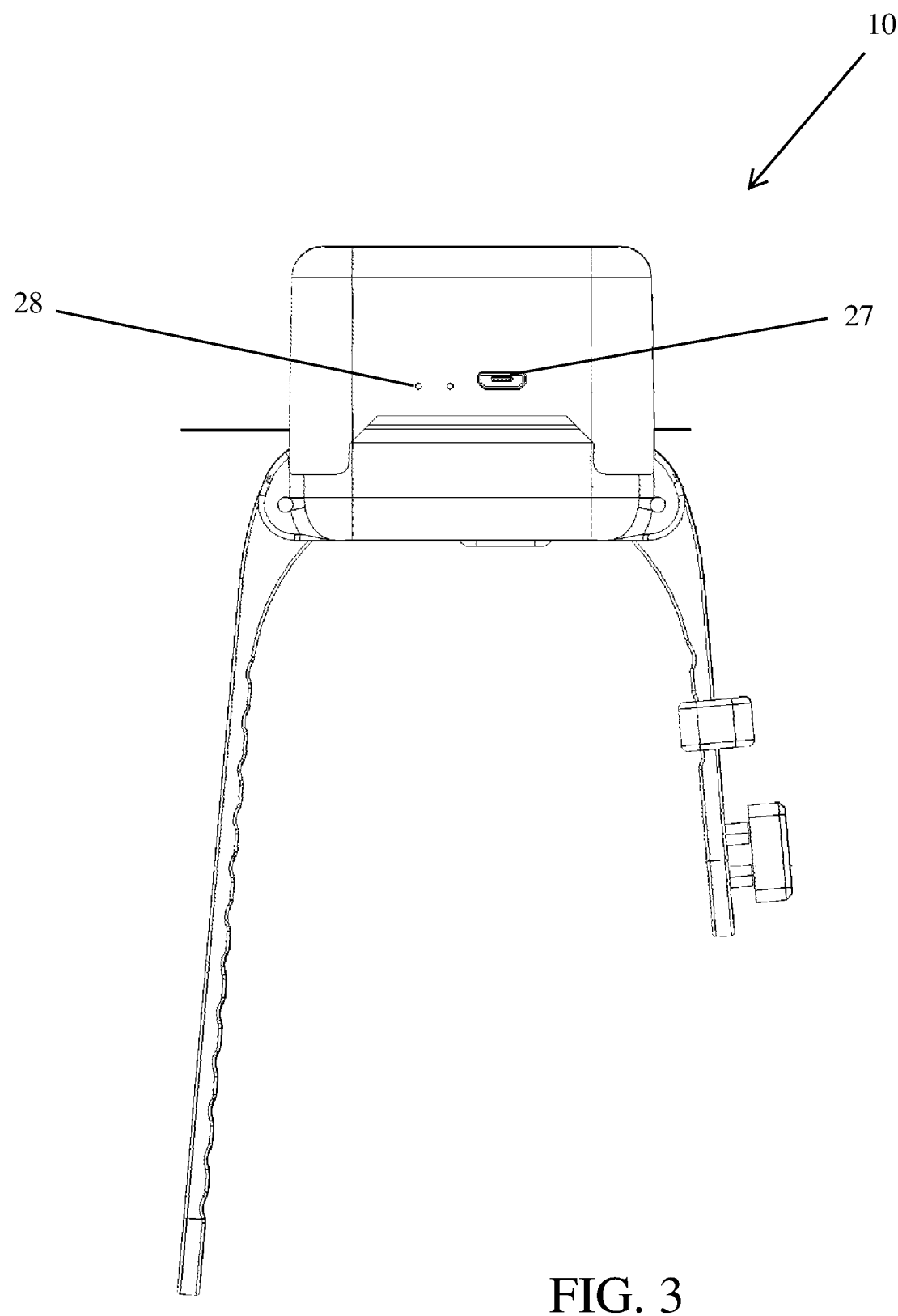
FIG. 3 is a front view of a watch embodiment of the present invention wherein the charging station is attached to the watch.
Figure 4:
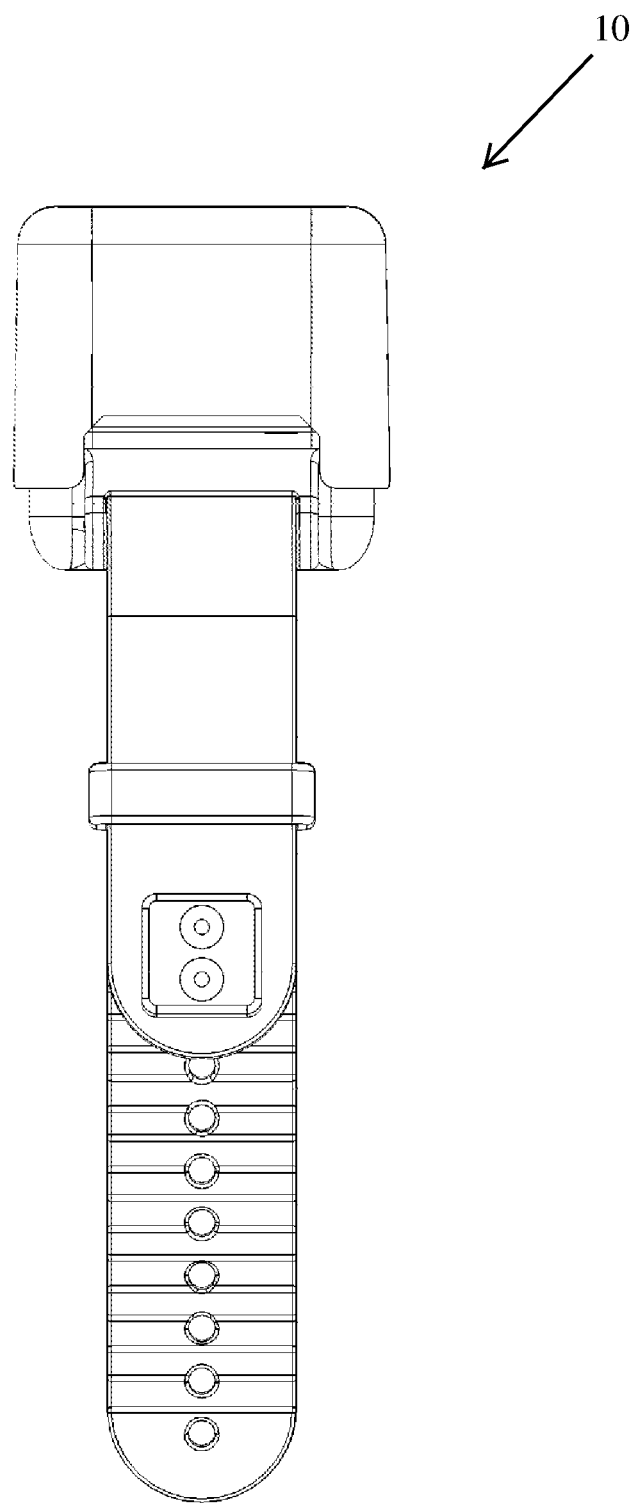
FIG. 4 is a right side view of a watch embodiment of the present invention wherein the charging station is attached to the watch.
Figure 5:
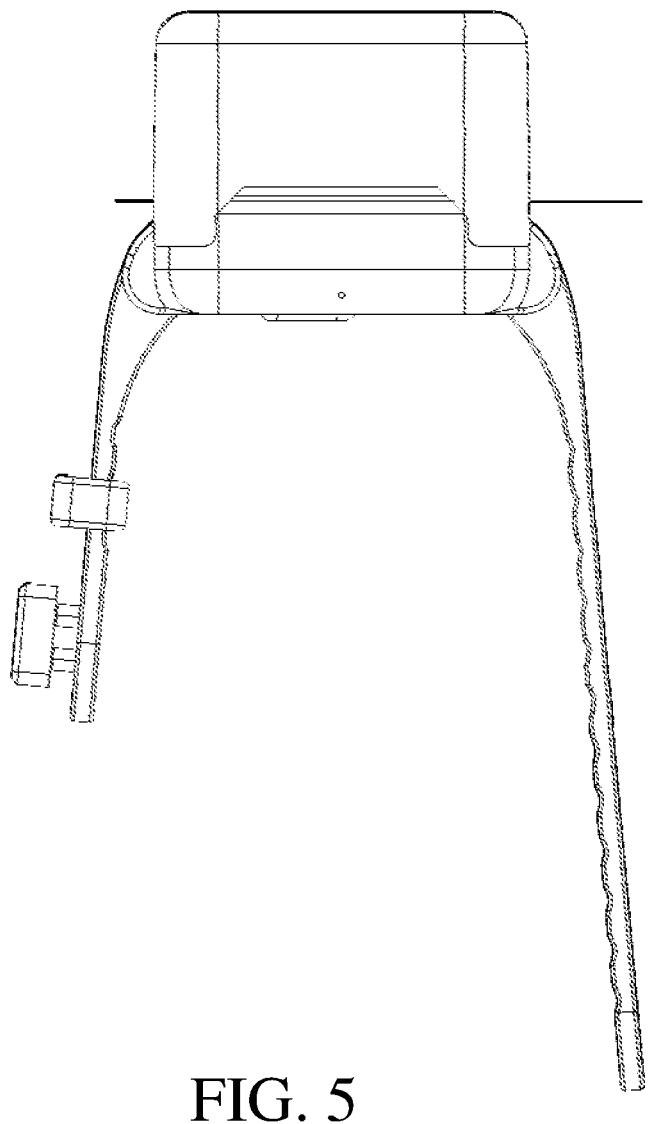
FIG. 5 is a rear view of a watch embodiment of the present invention wherein the charging station is attached to the watch.
Figure 6:
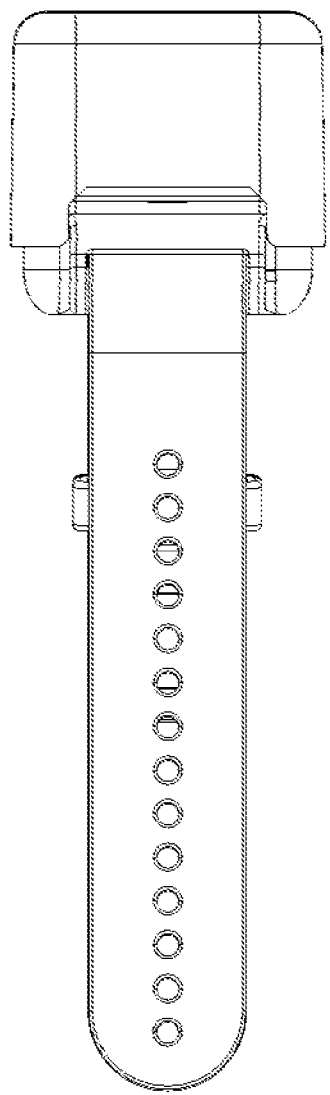
FIG. 6 is a left side view of a watch embodiment of the present invention wherein the charging station is attached to the watch.
Figure 7:
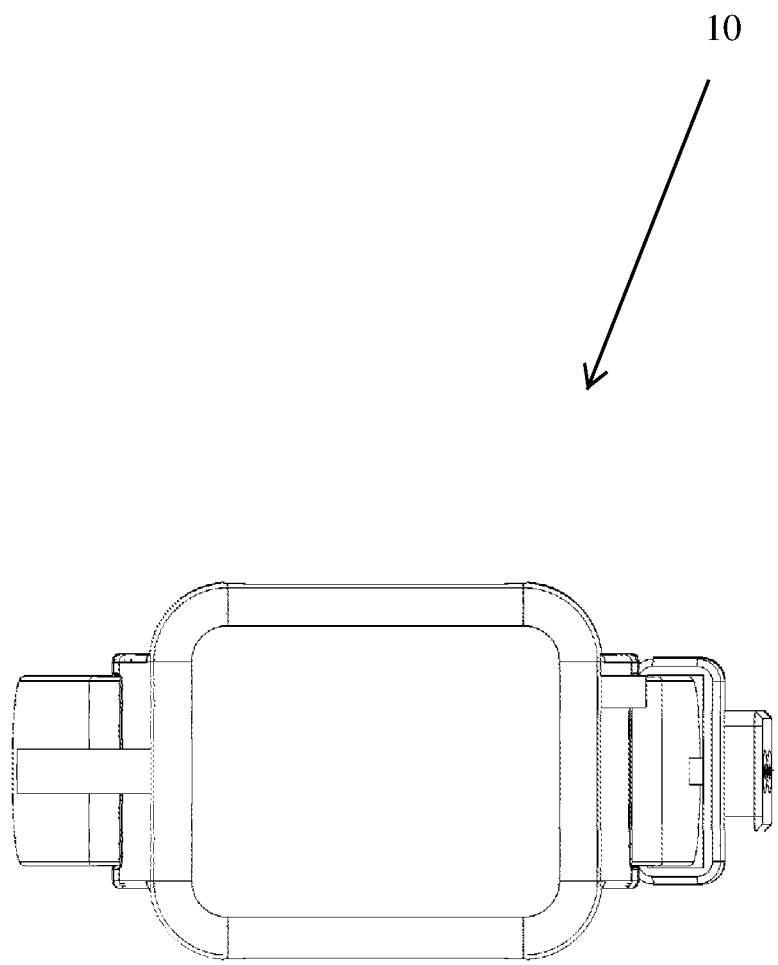
FIG. 7 is a top view of a watch embodiment of the present invention wherein the charging station is attached to the watch.
Figure 8:
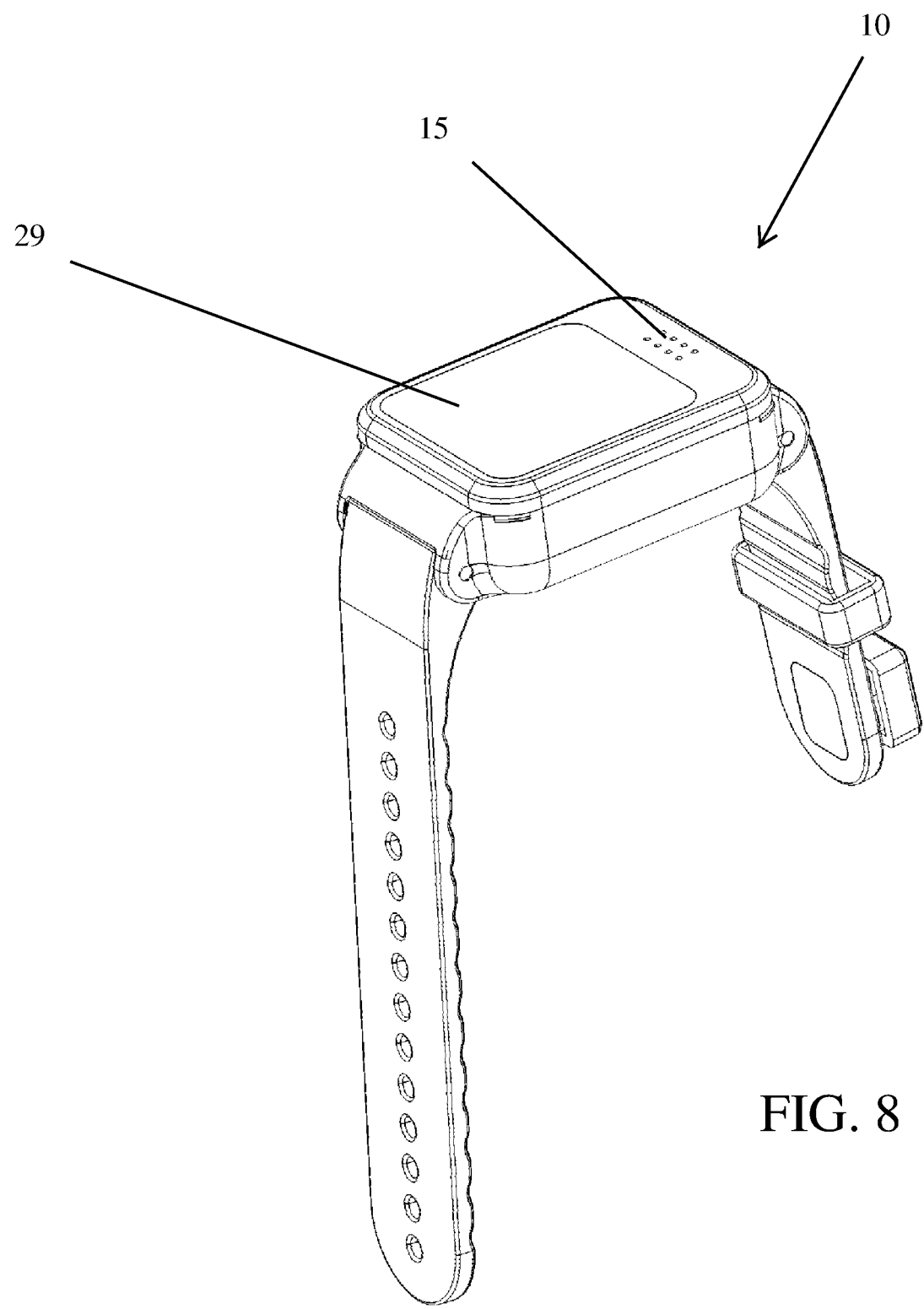
FIG. 8 is a side perspective view of a watch embodiment of the present invention wherein the watch is removed from the charging station.
Figure 9:
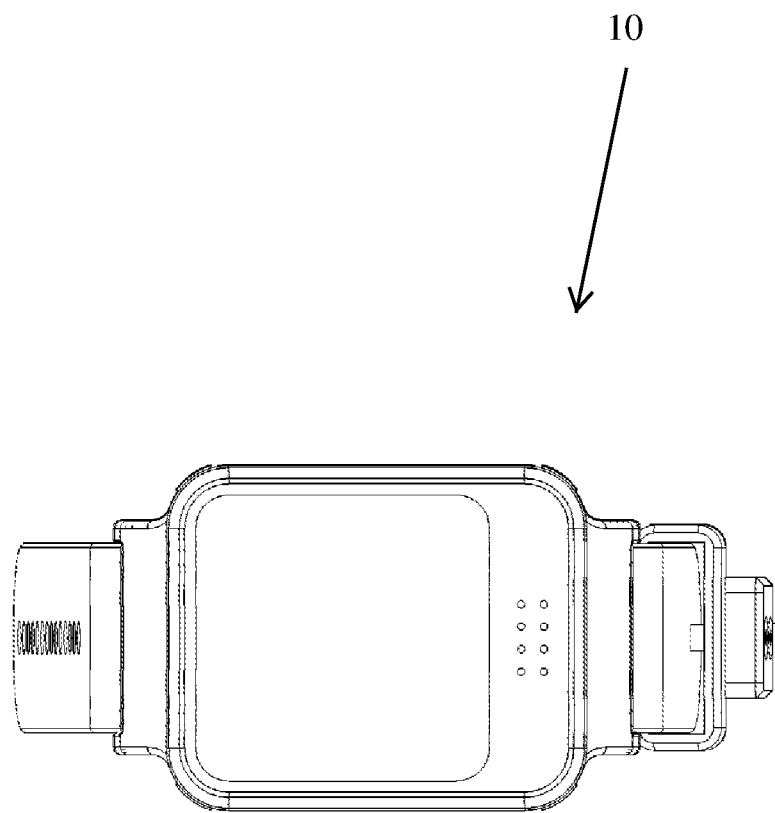
FIG. 9 is a top view of a watch embodiment of the present invention wherein the watch is removed from the charging station.
Figure 10:
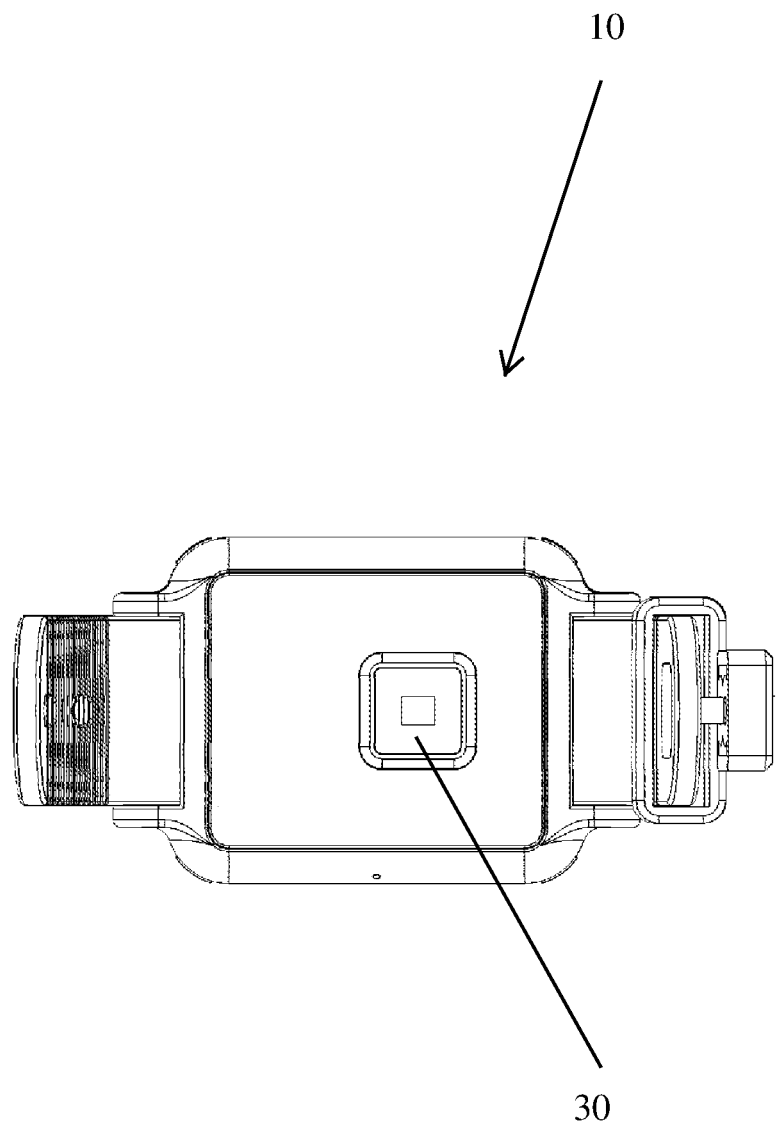
FIG. 10 is a bottom view of a watch embodiment of the present invention wherein the watch is removed from the charging station.
Figure 11:
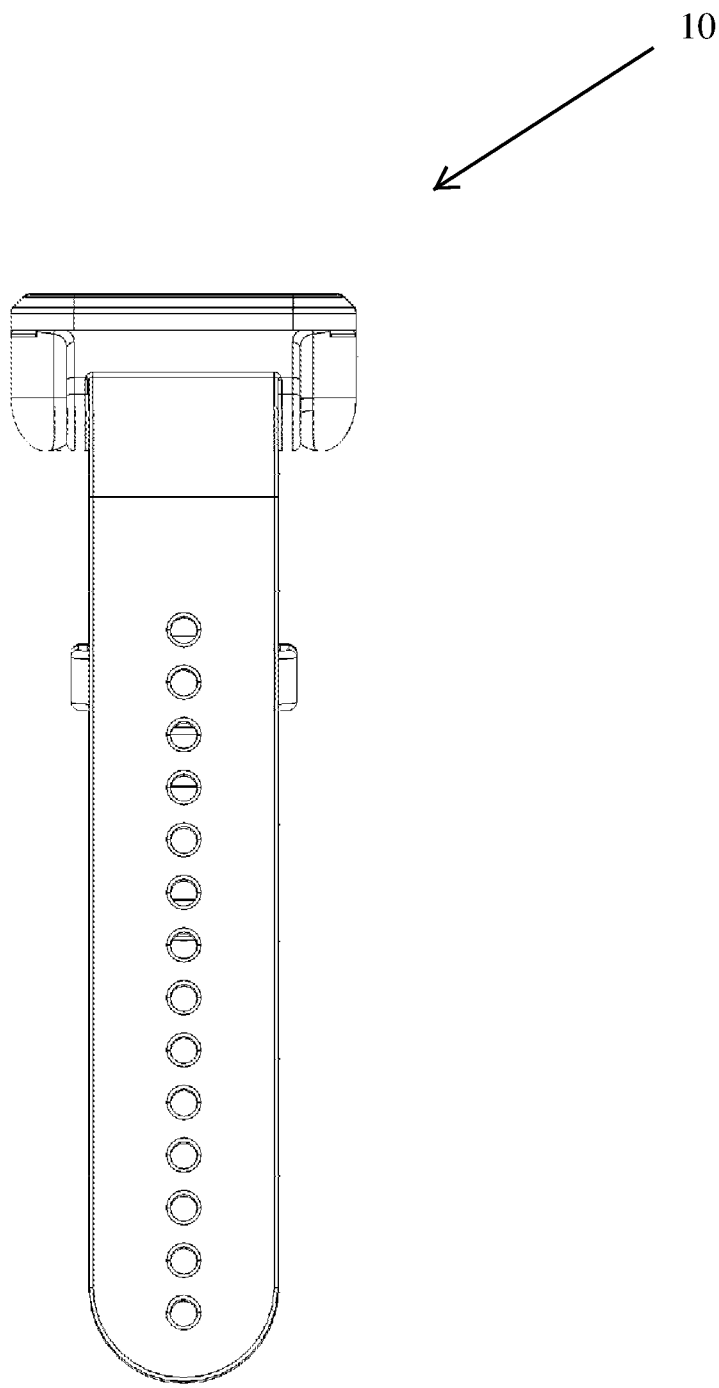
FIG. 11 is a left side view of a watch embodiment of the present invention wherein the watch is removed from the charging station.
Figure 12:
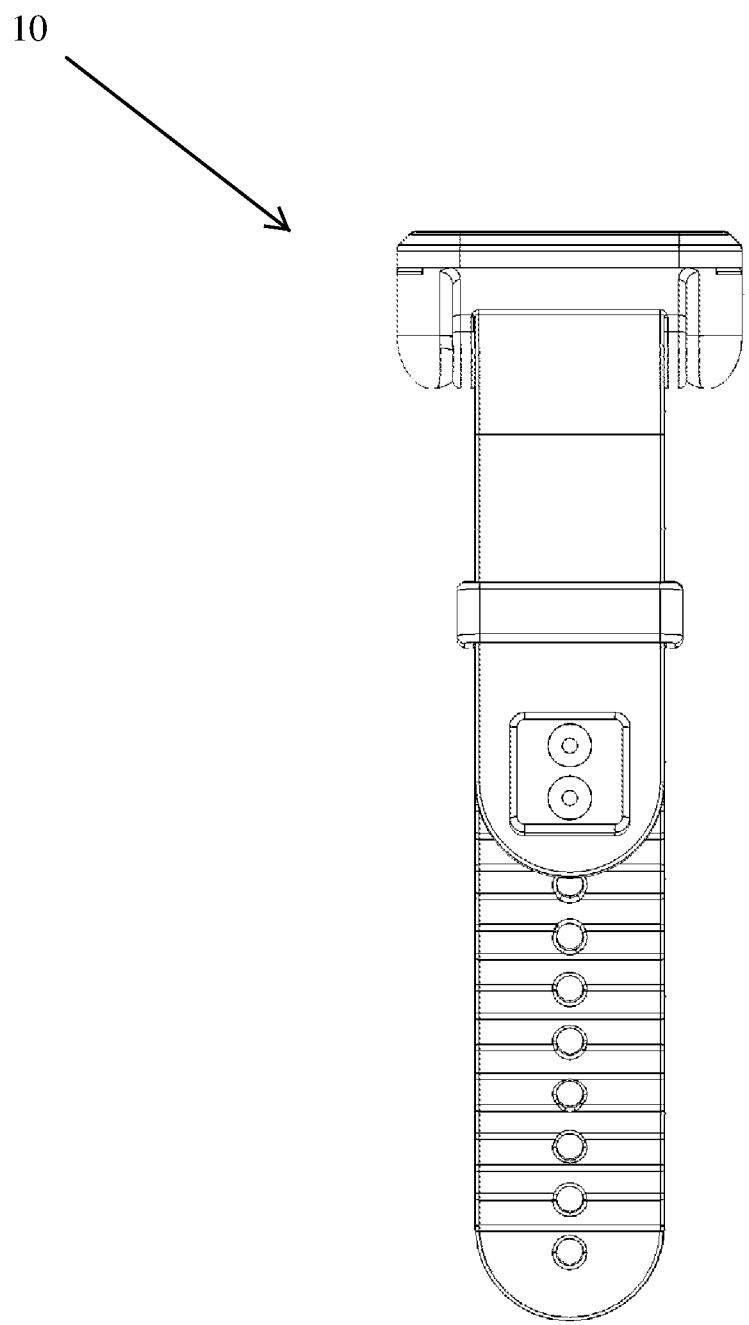
FIG. 12 is a right side view of a watch embodiment of the present invention wherein the watch is removed from the charging station.
Figure 13:
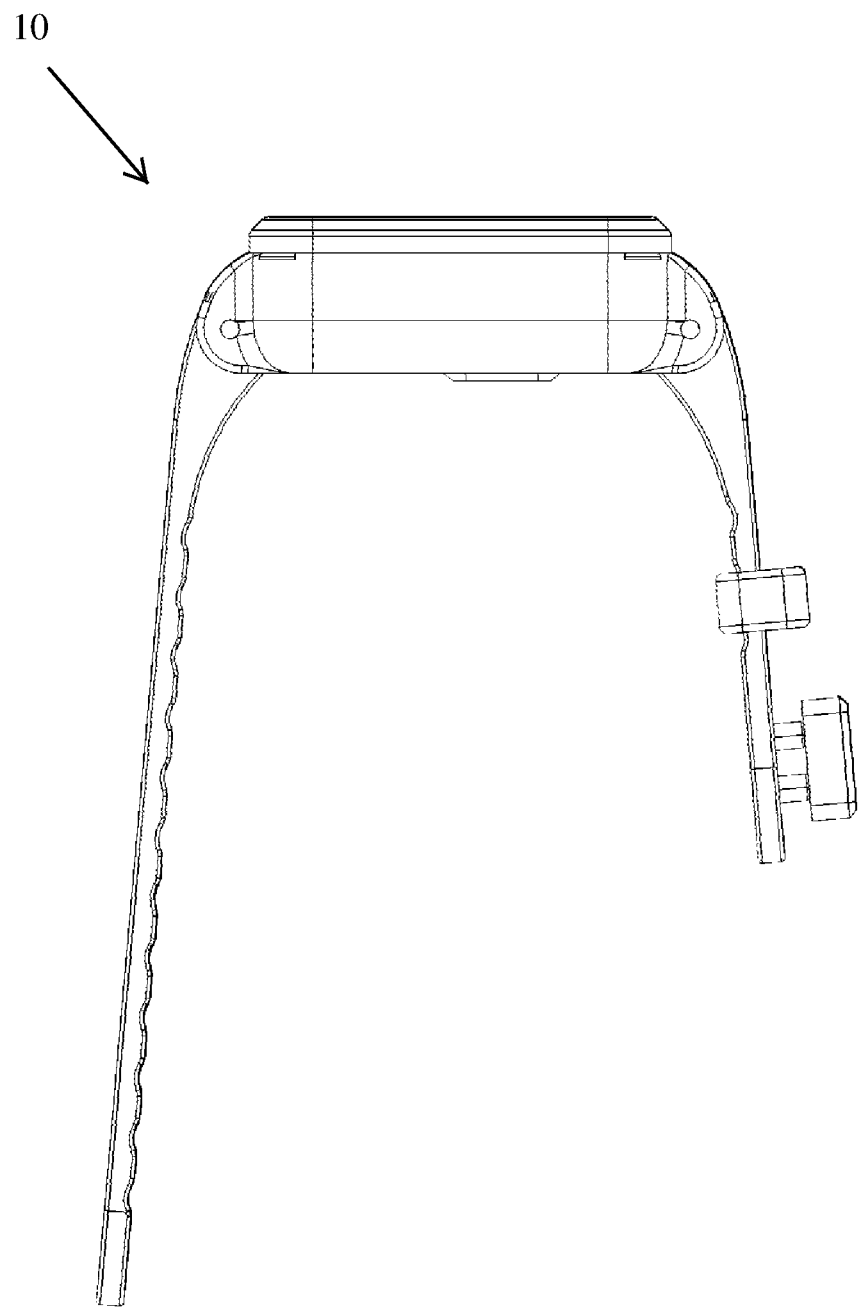
FIG. 13 is a front view of a watch embodiment of the present invention wherein the watch is removed from the charging station.
Figure 14:
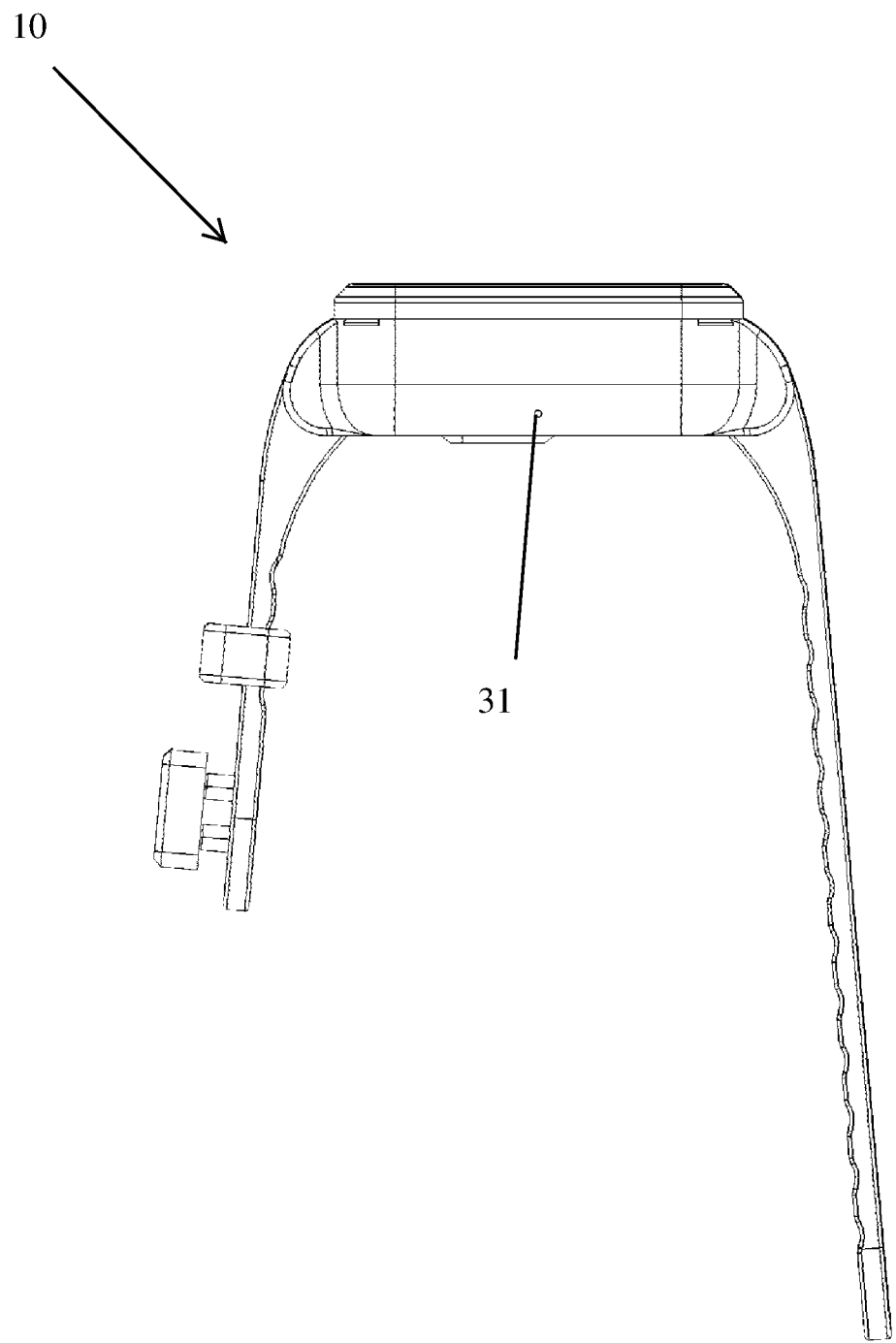
FIG. 14 is a rear view of a watch embodiment of the present invention wherein the watch is removed from the charging station.
Figure 15:
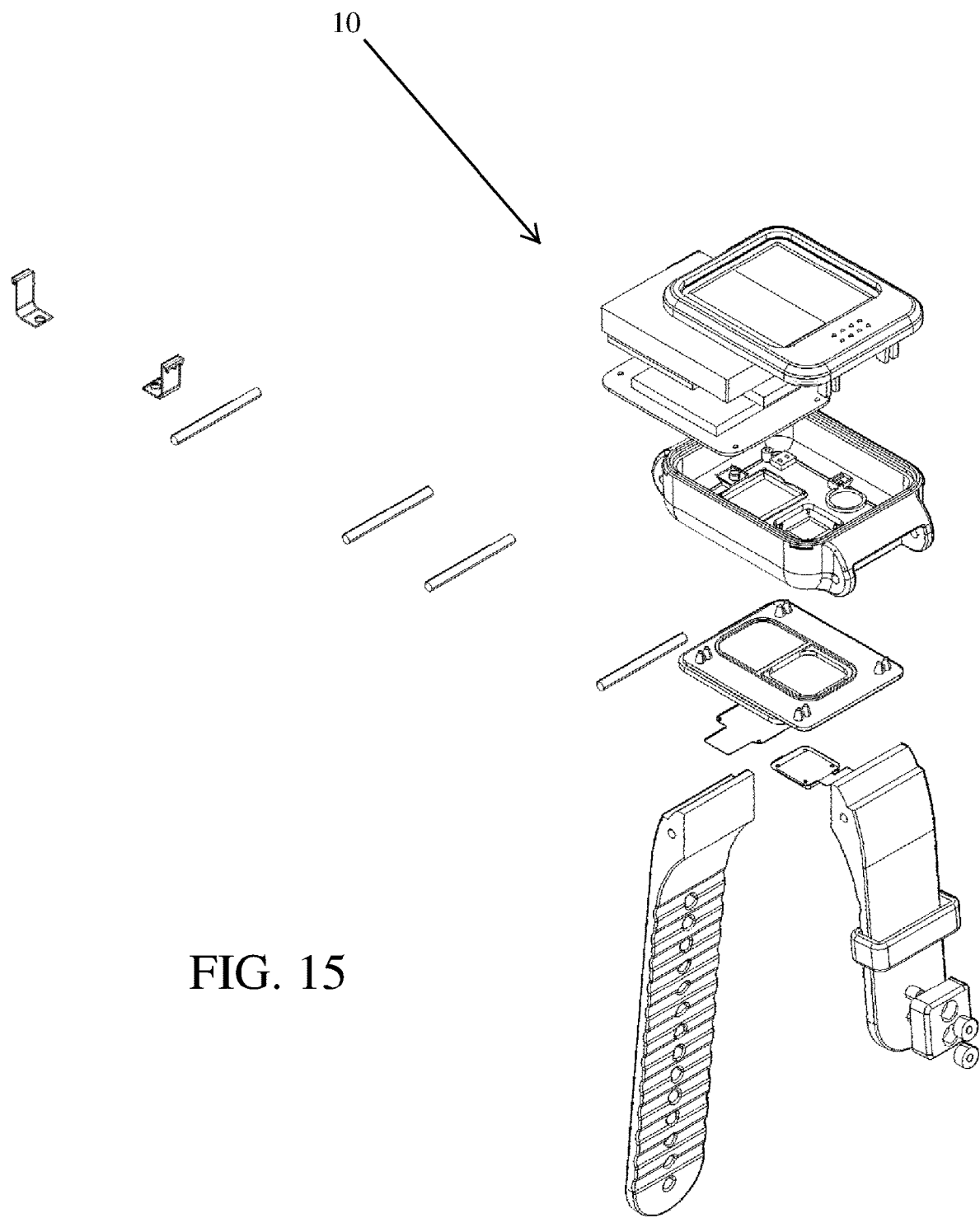
FIG. 15 is a perspective exploded view of a watch embodiment of the present invention wherein the watch is removed from the charging station.
Figure 16:
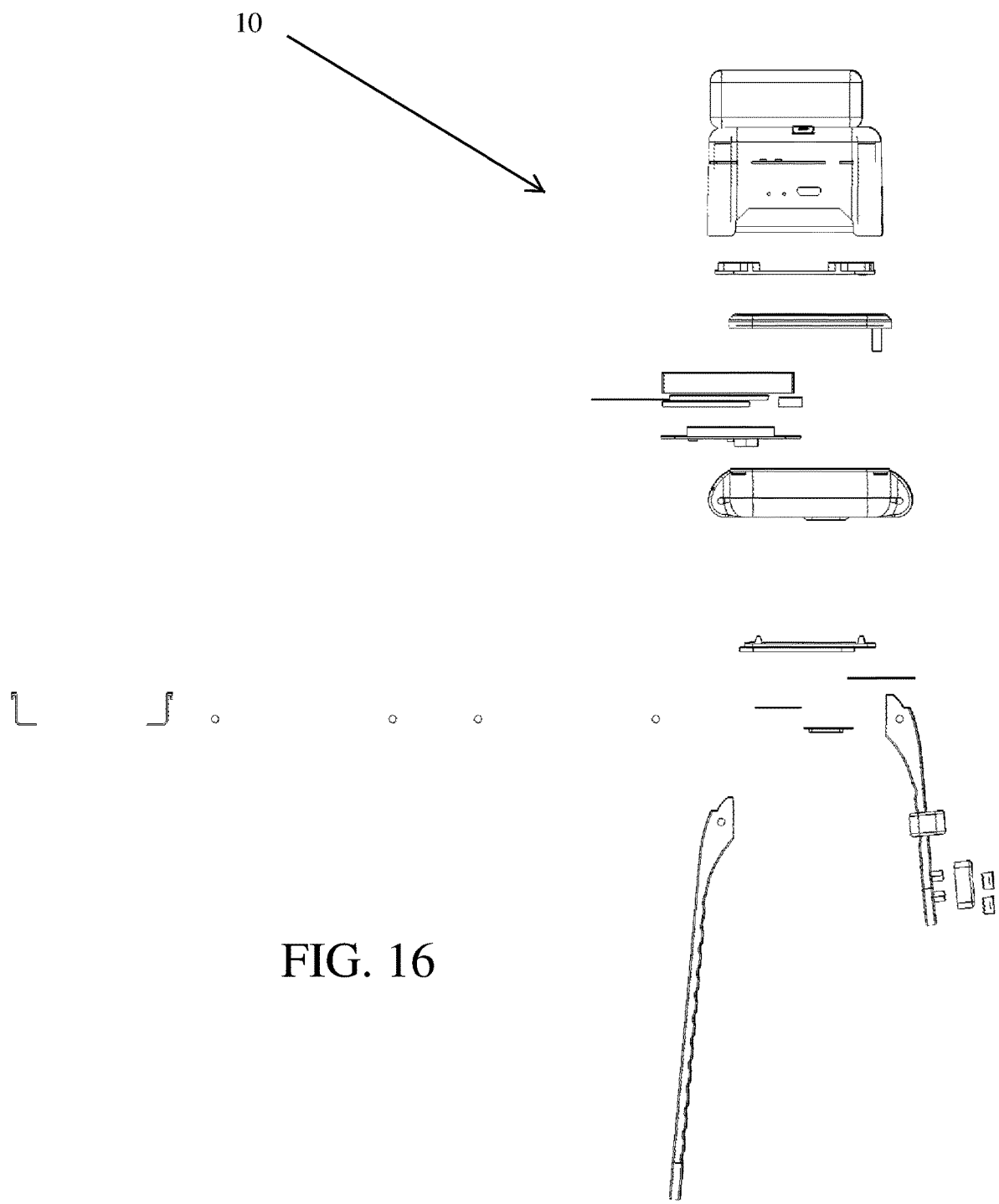
FIG. 16 is a side exploded view of a watch embodiment of the present invention wherein the watch is removed from the charging station

The present invention also includes a watch as shown in FIGS. 1-16. It can be used with the method and system described above. Preferably, the watch is sized for fitting comfortably on a human user's wrist or ankle. However, other suitable means of attaching the watch to the user can be used.

The smartwatch can have the features as described above when referring to the mobile device or smartphone.

In various embodiments of the present invention, the smartwatch incorporates features described in this specification, including but not limited to one or more of the following features: Wi-Fi, GPS receiver; Network location technology; color display; tamperproof band; tamperproof watch; water-proof; motion sensors; vibration alerts; messaging; heart rate detection; blood pressure detection; ability of user to communicate with participant by using two-way voice or electronic messaging; QR activation allowing convenient and effortless activation process for users in the field; management through ShadowtrackONE™ total corrections platform; inductive charging; IP67 waterproof rating; ability to call emergency personnel; send notifications; two-way facial recognition; light sensor; software to permit biometric identification of individual wearing device; software to permit communication between device and third party or third party device; camera; microphone; interactive screen; a panic alert button; interior tracking, which is the ability to track individuals within a structure using wifi technology when GPS is not available as well as the ability to alert the user if an enrollee has a low battery on the ShadoWatch device or if the ShadoWatch device has been turned off or the battery has died.

In one or more embodiments, the ShadoWatch™ supervisor is notified any time there is a change in monitoring status of the user. In one or more embodiments, notifications are sent to a user when the participant arrives at work, school or any other location where additional arrival verification, either at one location or through a building, is necessary.

Using the ShadoWatch™ device as shown in FIGS. 1-16, the Shadowtrack® platform can be used to help reduce the risk of an abduction typical in certain foreign countries. For example, in the event of a hostage attempt, The ShadoWatch™ device will establish communication with the central monitoring facility to alert trained operators of the hostage attempt in progress. An alert is generated either by the victim, a tamper is detected by the device or the victim is outside of their safe zone. Once communication is established, the central station operator will ask the victim if they are okay via the two-way-voice function of the device. If the victim is in a hostage situation and responds by saying that all is okay, the operator will respond by asking them what their secret passphrase is. The victim has the option of responding with the phrase associated with a false alarm and that all is okay or a phrase associated with an actual kidnapping or hostage event. If the phrase matches the hostage passphrase on file, the operator will respond with by stating, "thank you Mr. or Mrs. Jones, I have verified your passphrase is correct, have a good day." In the meantime, authorities will have been dispatched.

An embodiment of the present invention may include one or more of the following features:

- Ability to initiate on demand requests for voice verification, interviews, location verification, facial recognition, and sobriety
- Ability to send notifications via test to speech, text, email, and voicemail
- Ability to schedule one time and recurring notifications to one or multiple participants
- Ability to integrate agencies caseload management systems
- Automated email compliance notifications at the frequency the user desires
- Ability to transfer one or more users to another entity
- Ability to mass transfer one or more participants to another user or entity
- Multiple custom schedule templates for fast and easy participant enrollments
- Automatic transcription of audio recording
- Multiple reports library as well as custom reports
- Ability to view future scheduled events up to ninety days (90) in advance
- Ability to create tasks for both users and participants
- Custom protocols
- Unlimited number of interview questions
- Interview questions available in any language
- Automated interview reminders
- Participant mobile App
- User (Officer) mobile App
- Ability to locate one or multiple participants via the ShadoWatch™
- Facial recognition in the event of a voice verification failure
- Ability to view location tracking history via a map with location coordinates
- Offender pay solution
- Integration with lab or testing facilities Also incorporated herein by reference are my U.S. patent application Ser. No. 16/041,490, filed 20 Jul. 2018, and my U.S. Provisional Patent Application Ser. No. 62/534,961, filed 20 Jul. 2017.

PARTS LIST

The following is a list of parts and materials suitable for use in the present invention:

| Parts Number | Description |
|---|---|
| 10 | apparatus of a preferred embodiment of the present invention |
| 11 | battery (of the charging unit) |
| 12 | body casing (of the charging unit) |
| 13 | motherboard and inductive charger (of the charging unit) |
| 14 | watch screen cover |
| 15 | speaker |
| 16 | casing of watch body |
| 17 | strap of tamper resistant band |
| 18 | clasp of anti-dismantling device (metal, for example) |
| 19 | tamper proof screw cap of anti-dismantling device |
| 20 | strap of tamper resistant band |
| 21 | bracket to hold tamper resistant band to the casing of the watch body |
| 22 | pinrod to attach tamper resistant band to the body casing of the watch (metal, for example) |
| 23 | battery |
| 24 | mother board |
| 25 | mother board |
| 26 | sim card |
| 27 | charging port |
| 28 | charging light indicators |
| 29 | touch screen |
| 30 | sensor |
| 31 | microphone |

All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the following claims.

The invention claimed is:

1. A system for helping to prevent kidnapping, comprising:
   - a computer network;
   - a central monitoring facility;
   - a communications network; and
   - a communication device,
   - wherein the communication device is a mobile device comprising:
   - a global positioning system (GPS) receiver;
      - a wireless telephone communicator;
      - a casing which is water resistant
      - a light sensor;
      - a heart rate sensor;
      - a tamper proof band;
      - a wireless charger;
      - a screen;
      - a speaker;
      - a microphone;
      - software to permit biometric identification of individual wearing device;
      - software to permit communication between device and third party or third party device;
      - a camera; and
      - a panic alert button;
   - wherein the device establishes communication with the central monitoring facility when a triggering event takes place; and
   - wherein the establishment of communication between the device and the central monitoring facility alerts trained operators of a potential hostage attempt/kidnapping in progress.

2. The system of claim 1 wherein the casing of the mobile device is waterproof.

3. The system of claim 1 wherein the casing of the mobile device is waterproof to at least 3 meters.

4. The system of claim 1 wherein the screen of the mobile device comprises an interactive interface.

5. The system of claim 1 wherein the communication is voice communication.

6. The system of claim 1 wherein the communication is not voice communication.

7. The system of claim of claim 1 wherein the device further comprises the ability to engage in interior tracking.

8. The system of claim 1 wherein the screen of the mobile device comprises an interactive interface.

9. A system for helping to prevent kidnapping, comprising:
 a computer network;
 a central monitoring facility;
 a communications network; and
 a communication device,
 wherein the communication device is a mobile device comprising:
 a global positioning system (GPS) receiver;
  a wireless telephone communicator;
  a casing which is water resistant
  a light sensor;
  a heart rate sensor;
  a tamper proof band;
  a wireless charger;
  a screen;
  a speaker;
  a microphone;
  software to permit biometric identification of individual wearing device;
  software to permit communication between device and third party or third party device;
  a camera; and
  a panic alert button;
 wherein the device establishes communication with the central monitoring facility when a triggering event takes places;
 wherein the triggering event comprises an alert generated by a kidnapping victim, a detection of tampering by the device, or detection that the victim or device is outside of a pre-determined safe zone; and
 wherein once communication is established, a central station operator asks the victim if they are okay via a two-way voice function of the device and if the victim responds they are okay, the operator will respond by asking them what their secret passphrase is; wherein the victim has an option of responding with a phrase associated with a false alarm that all is okay or a phrase associated with an actual kidnapping or hostage event; wherein if the phrase stated by the victim matches the passphrase on file, the operator will respond by thanking the victim and stating that they have verified the passphrase, and to have a good day; wherein authorities are dispatched once victim responds with passphrase on file.

10. The system of claim 9 wherein the casing can work for at least work for at least 30 minutes while under up to 1 m of water.

11. The system of claim 9 wherein the device further comprises the ability to engage in interior tracking.

12. The system of claim 9 wherein the communication is voice communication.

13. A method of supervising an offender or defendant who has been arrested or incarcerated and then released, comprising the steps of:
 a) issuing to the offender or defendant a smart device comprising:
  a global positioning system (GPS) receiver;
  a wireless telephone communicator;
  a casing which is water resistant
  a light sensor;
  a heart rate sensor;
  a tamper proof band;
  a wireless charger;
  a screen;
  a speaker;
  a microphone;
  software to permit biometric identification of individual wearing device;
  software to permit communication between device and third party or third party device; and
  a camera;
 b) a monitoring entity monitoring the offender or defendant
 c) wherein the monitoring entity initiates on demand verification of the offender or defendant via communication with the smart device; and
 d) wherein a second entity that is a law enforcement entity is notified if the offender or defendant is not properly identified via the on demand verification.

14. The method of claim 13 wherein the device meets the standards of an IP67 waterproof rating.

15. The method of claim 13 wherein a supervisor is notified any time there is a change in monitoring status of the offender or defendant.

16. The method of claim 13 wherein the offender or defendant is apprehended by the law enforcement entity after receiving the notification that the offender or defendant has not been properly identified via the on demand verification.

17. The method of claim 13 wherein the device further comprises the ability to engage in interior tracking.

18. The method of claim 13 wherein the screen of the smart device comprises an interactive interface.

19. The method of claim 13 wherein the communication is voice communication.

20. The method of claim 13 wherein the communication is not voice communication.

* * * * *